United States Patent [19]
Khanwilkar et al.

[11] Patent Number: 6,074,180
[45] Date of Patent: Jun. 13, 2000

[54] HYBRID MAGNETICALLY SUSPENDED AND ROTATED CENTRIFUGAL PUMPING APPARATUS AND METHOD

[75] Inventors: Pratap S. Khanwilkar, Salt Lake City, Utah; Paul E. Allaire, Charlottesville, Va.; Gill Brent Bearnson; Don B. Olsen, both of Salt Lake City, Utah; Eric H. Maslen, Earlysville, Va.; James W. Long, Salt Lake City, Utah

[73] Assignees: Medquest Products, Inc.; University of Utah Research Foundation, both of Salt Lake City, Utah; University of Virginia Patent Foundation, Charlottesville, Va.

[21] Appl. No.: 08/850,598

[22] Filed: May 2, 1997

Related U.S. Application Data

[60] Provisional application No. 60/016,856, May 3, 1996.

[51] Int. Cl.[7] ............................ F04B 17/00
[52] U.S. Cl. .............. 417/356; 417/423.7; 417/420; 415/900
[58] Field of Search .................. 417/356, 423.7, 417/420; 415/900; 416/3, 186 R, 188

[56] References Cited

U.S. PATENT DOCUMENTS

| | | | |
|---|---|---|---|
| 4,688,998 | 8/1987 | Olsen et al. | 417/356 |
| 5,044,897 | 9/1991 | Dorman | 417/423.7 |
| 5,055,005 | 10/1991 | Kletschka | 417/356 |
| 5,112,202 | 5/1992 | Oshima et al. | . |
| 5,195,877 | 3/1993 | Kletschka | 417/356 |
| 5,685,700 | 11/1997 | Izraelev | 417/423.7 |
| 5,840,070 | 11/1998 | Wampler | 417/423.7 |

*Primary Examiner*—Charles G. Freay
*Assistant Examiner*—Cheryl J. Tyler
*Attorney, Agent, or Firm*—Thorpe, North & Western, LLP

[57] ABSTRACT

An apparatus and method for a centrifugal fluid pump for pumping sensitive biological fluids, which includes (i) an integral impeller and rotor which is entirely supported by an integral combination of permanent magnets and electromagnetic bearings and rotated by an integral motor, (ii) a pump housing and arcuate passages for fluid flow and containment, (iii) a brushless driving motor embedded and integral with the pump housing, (iv) a power supply, and (v) specific electronic sensing of impeller position, velocity or acceleration using a self-sensing method and physiological control algorithm for motor speed and pump performance based upon input from the electromagnetic bearing currents and motor back emf—all fitly joined together to provide efficient, durable and low maintenance pump operation. A specially designed impeller and pump housing provide the mechanism for transport and delivery of fluid through the pump to a pump output port with reduced fluid turbulence.

34 Claims, 19 Drawing Sheets

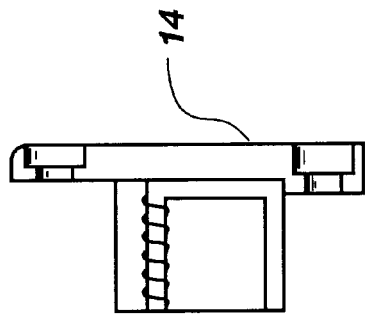
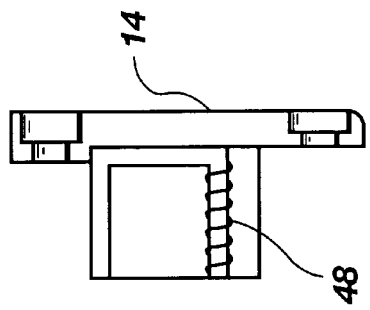
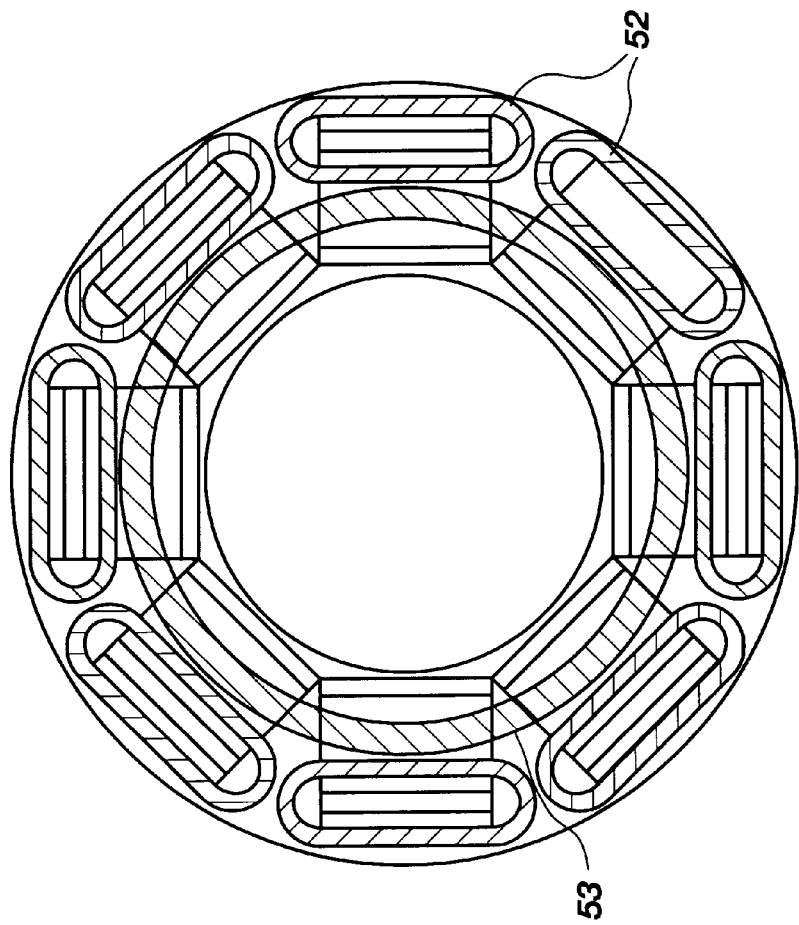

HYBRID MAGNETICALLY SUSPENDED AND ROTATED CENTRIFUGAL PUMPING APPARATUS AND METHOD

This application claims benefit of provisional application Ser. No. 60/016,856 entitled "HYBRID MAGNETICALLY SUSPENDED AND ROTATED CENTRIFUGAL PUMPING APPARATUS AND METHOD," filed May 3, 1996.

BACKGROUND OF THE INVENTION

1. The Field of the Invention

This invention relates to magnetically supported and rotated rotors and, more particularly, to a centrifugal pumping apparatus and method whose disk-like impeller is magnetically suspended and rotated in a contact-free manner, the rotation speed of the impeller being controlled and changed electronically by fluid pressure and impeller positioning algorithms.

2. The Background Art

Historically, fluid pumps are of many and varied types and configurations, all performing essentially the same end result, namely, to provide fluid movement from one point to another. All pumps have a similar characteristic in that fluid is drawn into the pump through a vessel or pipe by a vacuum created by pump operation. In addition to the primary force of vacuum, secondary forces such as gravity, impeller inertia, or existing pipe/vessel fluid pressures also have an effect on fluid flow. Operation of the pumping mechanism creates a fluid pressure and/or fluid velocity which subsequently creates the vacuum that draws fluid into the pump through a pump inlet port. Fluid from the inlet port is transported throughout the pump by the pump mechanism which subsequently directs fluid to a pump outlet port.

Fluid pump configurations vary mostly by adaptation to function. For example, lift and force pumps utilize a reciprocating motion to displace fluid, whereas vacuum pumps create a vacuum that is used to displace fluid. Rotating axial-flow pumps utilize propeller-like blades attached to a rotating shaft to accomplish the displacement of fluid. Jet pumps utilize a steam-jet ejector which enters a narrow chamber inside the pump and crates a low-pressure area that correspondingly creates a suction that draws the fluid into the chamber from an inlet port. Although, other pump types could be specified, more specific reference will be made hereafter to fluid pumps for a sensitive fluid such as blood which are more easily adaptable to environments where size and geometry of the pump are critical.

The rotating centrifugal pump is, by nature, more tightly configured and readily adaptable to pumping of sensitive fluids. Blood flow pumps have relatively low flow rate performance characteristics compared to many ordinary industrial applications yet have significant pressure rise requirements. Centrifugal pumps are well suited to such applications rather than axial flow pumps or other designs. This leads to the use of a centrifugal pump design for the preferred embodiment of this invention. The pump includes several ribs or vanes mounted to an impeller whose rotational force impels fluid toward the outside of the rotor by centrifugal force. Centrifugal pumps traditionally possess a shaft-mounted impeller immersed in the fluid, where the shaft extends through a seal and bearing apparatus to a drive mechanism. Revolving vanes of the impeller create a partial vacuum near the center of the axis of rotation which correspondingly draws in fluid through the intake opening of the pump. A smooth pump volute is located in the pump stationary component to assure the smooth flow of pumped fluid from the exit of the impeller to the pump exit passage. The volute accumulates the pump flow as it exits the pump impeller and performs the function of increasing the fluid pressure (head) by converting fluid kinetic energy (velocity) to potential energy (pressure or head). Although centrifugal pumps do not require valves for movement of fluid, pump geometry must be such that fluid drawn in through the input opening will continue through the pump mechanism and on to the outlet port without significant internal fluid leakage or inefficiencies.

These prior art pumps are known to have problems. For example, it is well documented that shaft seals as configured in conventional centrifugal pumps are notoriously susceptible to wear, failure, and even attack by certain fluids, thus resulting in leakage problems. It is also well known that pumps for some fluids require more careful design consideration and require specific pumping techniques in order to avoid fluid damage, contamination, and other undesirable conditions. For example, fluids such as corrosive fluids (acids or caustics) or sensitive fluids such as blood, require special consideration such that seals do not leak and thereby lose integrity of the fluid. Pumping of sensitive fluids, such as blood, by continuous flow pumps requires highly reliable and non-damaging bearings to support the rotating impeller. Prior art pumps have very significant problems with bearings needed to support the impeller as it rotates. Ball and other rolling element bearings can only be employed if isolated from the sensitive fluid (blood) by shaft seals and lubricated with non-body fluids. In this situation, all of the sealing problems indicated above apply. If the conventional ball or other rolling element hearings employ the sensitive fluid as a lubricant, the sensitive fluid living properties, such as red blood cells in blood, are destroyed in a short period of time due to being ground between the rolling components in the bearings. Thrust and radial fluid film bearings, lubricated with the sensitive fluid, have been employed in some prior art pumps. These have been subject to poor performance and/or many failures due to seizure of the rotating component in the stationary component, production of thrombosis (clotting), damage to the sensitive fluid due to hemolysis (high shear), and other problems. Fluid film bearings also do not provide any information on the instantaneous pump pressures and flow rates that can be employed for speed control of the motor to match physiological needs to future pump performance. Conventional ball bearings and fluid film thrust and radial bearings do not have the long term reliability required for pumps in which fluid stasis and high fluid shear stress must be avoided, such as blood pumps. Furthermore, ball bearings have a limited life when employed in the pumping of sensitive fluids and often must be lubricated by an external lubricating fluid which requires seals to contain the lubricating fluid. Transport and containment of lubricating fluid for bearings increases the overall size of the pump housing as well as increasing complexity of operation due to extra vessels and mechanisms used to deliver and cool lubricating fluid, thereby making pump apparatus non-implantable if used to replace natural heart functions. Therefore, the relatively short life of fluid pumps with shafts and conventional bearings makes them unsuitable for implanting in body cavities for the long term replacement of natural heart functions.

Furthermore, pumping of blood involves specific known hazards typically associated with shaft seals for impeller-type blood pumps due to pockets of fluid being susceptible to stagnation and excessive heat. Further still, pumping sensitive fluids, such as blood, requires careful consideration of geometry of impeller vanes and pump housing. Excessive mechanical working and heating of blood causes blood components to breakdown by hemolysis and protein denaturization, which leads to blood coagulation and thrombosis.

Avoidance of blood damaging effects of pump operation is best accomplished by natural heart function. The natural heart has two basic functions, each side performing a different pumping function. The right side of the natural heart receives blood from the body and pumps it to the lungs, whereas the left side of the natural heart collects blood from the lungs and pumps it to the body. The beating of the natural heart, in combination with heart valves, provides blood pumping action in a pulsatile, remarkably smooth and flowing manner. Blood flow (cardiac output) of the natural heart is primarily regulated by venous return, otherwise known as pump preload. However, due to diseases or accident, natural heart functions can be partially or totally lost. Mechanical apparatus developed to replace natural heart functions historically ranged in size from extremely large in the earliest heart-lung or pump oxygenator apparatus to more recent apparatus whose size and function more closely resembles that of the natural heart.

In addition to total heart replacement, development of other mechanical apparatus focuses on replacement of a portion of the function of the natural heart, such as a ventricular assist device that aids a failing left ventricle weakened by disease or other damage. A primary consideration for natural heart function replacement, whether partial or total, is that blood must be pumped throughout the entire apparatus in a gentle, low thermal, and non-destructive manner. For example, if a pump impeller supported by mechanical bearings comes in contact with blood, relative movement between parts of the bearings results in excessive mechanical working of the blood which causes blood cells to rupture, resulting in hemolysis. Another mechanical effect that can injure blood is formation of regions within the pump where blood is semi-stagnant or where blood will eddy without sufficient blood exchange, thereby creating the equivalent to blood stagnation. The result of blood stagnation often is coagulation of the blood (thrombosis), which correspondingly causes blood to cease to flow at all. Yet another effect that can injure blood is excessive heating due to friction of a sidewall of the pump or other pumping mechanisms as blood passes through the pump. Specifically, side wall friction caused by abrupt angular changes of internal pump geometry requires blood to follow harsh changes of direction and thereby creates excessive mechanical working of blood which causes blood cell rupture or activation of blood platelets and corresponding hemolysis and thrombosis. Yet another effect that can injure blood is caused by inefficient pump operation whereby a large part of the energy supplied to the pump appears as heat discharged into the blood which damages blood by overheating and coagulation. Notably, because blood albumen begins to denature at 42 degrees Centigrade, inefficiencies in pump operation which result in overheating of the blood will cause a very serious and life threatening condition.

The before mentioned conditions of stagnation, harsh pump geometry, turbulence and/or heating will activate blood platelets and/or damage oxygen-carrying red blood cells. Damage to blood starts a chain reaction that forms a thrombus with potential to block blood vessels, starving the tissues it nourishes, and leading to a serious, life threatening condition. Numerous attempts to avoid the foregoing problems associated with pumping blood have been made using flexible diaphragms and collapsible tubing in roller pumps. However, the continual flexing of the diaphragm and/or tubing material is known to change the blood-contacting properties of the material resulting in material fatigue, dislodged fragments of the internal wall of the flexible material, and emboli passed into the bloodstream by the fragments.

In addition to the above mentioned conditional requirements for pumping blood, the rate of impeller rotation has a significant effect on stability and structure of sensitive vessels. Impeller rotational operation that is not regulated by pump preload pressure will cause atrial suction in sensitive vessels just prior to the pump inlet port, wherein blood vessels collapse when impeller rotation exceeds blood vessel wall rigidity. Prior art pumping apparatus has not provided adequate integration of controls to insure that rapid adjustments to impeller rotational speed does not have a negative effect.

Kletschka '005 (U.S. Pat. No. 5,055,005) discloses a fluid pump levitated by opposing fluid. Stabilization of impeller by opposing fluid alone is not sufficient to maintain impeller in precise position within pump housing, as well as high pressure fluid jets subject blood to the before mentioned blood coagulation caused by mechanical working of blood.

Kletschka '877 (U.S. Pat. No. 5,195,877) discloses a fluid pump with a magnetically levitated impeller utilizing a rigidly mounted shaft surrounded by a magnetically levitated rotor which serves as an impeller for fluid. The shaft of this invention introduces a requirement for a hydraulic bearing and seal at the juncture of the shaft and the rotating impeller which subjects blood, or other sensitive fluids, to thermal and stagnation conditions at the region of the bearing.

For more than 25 years, those skilled in the art have studied pumps that are used as total artificial hearts and experimentally implanted in animals. These studies have provided useful feedback of the relative effectiveness of blood pumping apparatus. These pumps can be categorized a, producing pulsatile or non-pulsatile flows. The pumps producing pulsatile fluid motion (positive displacement pumps) more closely resemble fluid motion as provided by the natural heart. Information to date has not yet determined if pulsatile fluid movement is needed to provide a necessary physiological benefit, or if the pulsatile fluid motion is primarily due to the non-rotary nature of heart muscle. Most pulsatile pumps universally require valves (mechanical or tissue) with inherent mechanical problems and limitations. valve systems are not required in prior art non-pulsatile pumps, the non-pulsatile pumps require rotating shafts passing through various bearings and seals. These shafts create inherent problems of blood stagnation, contamination and undesirable thermal conditions, thereby making long term use of the pumps as a replacement for natural heart function unfeasible. Most early prior art rotating non-pulsatile systems were installed outside of the body for short-term cardiac assistance and experienced a moderate amount of success.

One blood pumping apparatus is the total artificial heart. The total artificial heart has been used in five patients as a permanent replacement for pathological, irreparable ventricles; and in 300 patients as a temporary bridge to cardiac transplantation. The longest support on the total artificial heart has been 795 days. Other blood pumping apparatus, e.g., ventricular assist devices, have been used in patients unweanable from cardiopulmonary bypass during cardiac surgery or those whose one ventricle only has failed. The most common mechanical replacement of natural heart function is a temporary bridge to cardiac transplantation by a ventricular assist device with over 1250 patients receiving such temporary ventricular assist apparatus.

Historically, blood pumping apparatus have presented many problems. For example, the pumping mechanism of reciprocating (diaphragm) total artificial hearts has been energized with gases (pneumatic systems), electricity (motors, solenoids, etc.), and skeletal muscles. The energy sources and associated convertor systems possess additional components that increase complexity of the total system and thereby contribute to overall unreliability. Also, the size of prior art systems for total artificial hearts is very restrictive to patient mobility and not conducive to quality of life of the recipient. Another constraining factor not fully met by prior art apparatus is that the excessive size and complexity of energy conversion systems, as well as overall pump design exceeds the available anatomical space. Furthermore, most of these prior art reciprocating systems exhibit excessively high (i) noise characteristics, (ii) vibration, and (iii) recoil (thrust) levels.

Many of the problems of the prior art rotating pumps have been addressed by those skilled in the art through pump adaptation with capability to meet the above mentioned requirements for pumping sensitive fluids (such as blood). These pump adaptations can be accomplished bag support of the impeller through electromagnets located on the impeller and the housing such that the impeller can be rotated without shafts, seals or lubricating systems. Permanent magnets without some form of additional support cannot entirely suspend an object, such as an impeller, but require additional adjustable support or force in some axis to achieve stabilized suspension. This is based on Earnshaw's theorem which indicates that suspension systems comprised solely of permanent magnets will not be stable. However, actively controlled electromagnets can be used to stabilize and support an object with respect to all degrees of freedom of movement. Additionally, one electromagnet with a feedback position sensor can provide stable suspension of an object (or impeller in the case of the centrifugal fluid pump). The only expenditure of energy in hybrid magnetically supported impellers is electromagnetic energy utilized for stabilizing and rotating the impeller. Permanent magnets and one electromagnet for impeller suspension and rotation create a stable and efficient pump operation.

Within the past decade, prior art patents have disclosed magnetically suspended and rotated rotors which have exhibited a limited degree of success. These prior art configurations utilize partial magnetic suspension to reduce hazards to blood. Although magnetically suspended prior art devices successfully reduce some of the friction hazard of the rotary shaft, the prior art devices are still impractical for implantation in total heart replacement due to size, complexity, and less than optimal impeller positioning, position sensing, and speed control. The excessive size and difficulty in maintaining precise impeller positioning and speed of these prior art inventions is due mostly to geometric configuration of the impeller, which is cylindrical, spherical, or otherwise mostly three dimensional in nature.

In view of the foregoing, it would be a significant advancement in the art to provide improvements in magnetically suspended and rotated centrifugal pumping apparatus to thereby allow for reduced size and increased accuracy in impeller positioning and speed controls. It would also be an advancement in the art to provide a centrifugal pumping apparatus that would be free of shafts, rolling element or fluid film bearings, mechanical seals, or physical proximity sensors, thereby allowing for a fully integrated pump design without mechanical contact, wear, failure due to seizing up of fluid bearings, and generation of thrombosis or shear damage. An even further advancement in the art would be to provide a centrifugal pumping apparatus with geometry of impeller and pump housing such as would provide efficient and low-turbulence transport of fluid throughout pump mechanisms including the pump output port. Further still, it would be an advancement in the art to provide a versatile centrifugal pumping apparatus that could operate in either pulsatile or non-pulsatile mode.

OBJECTS AND SUMMARY OF THE INVENTION

It is a primary object of the present invention to provide improvements in rotating centrifugal fluid pumps for sensitive fluids.

It is another object of the present invention to provide improvements in fluid pumps using a combination of permanent magnets, efficient non-contact electromagnetic bearings, and an efficient motor.

It is also an object of the present invention to provide a centrifugal pumping apparatus of relatively compact size to enable anatomical implantation.

It is a further object of the present invention to provide a centrifugal pumping apparatus and method to provide a long product life and which requires minimal maintenance.

It is an additional object of the present invention to provide improvements in centrifugal fluid pumps which are used for partial or total heart function replacement.

It is still another object of the present invention to provide a centrifugal pumping apparatus and method whose pump design geometry provides efficient and low-turbulence transport and output of sensitive fluid throughout the pump, including low-turbulence output just beyond the outlet port.

It is yet another object of the present invention to provide a centrifugal pumping apparatus and method whereby fluid pressure and output fluid volume are controlled and changed electronically via specific fluid pressure and positioning algorithms.

It is another object of the present invention to provide a centrifugal pumping apparatus and method that is capable of operation in either pulsatile or non-pulsatile mode.

It is yet another object of the present invention to provide a centrifugal pumping apparatus and method that is adaptable as either a ventricular assist device or paired to provide a total heart replacement.

The above objects and others not specifically recited are realized through an apparatus and method for a centrifugal fluid pump for pumping sensitive biological fluids, which includes (i) an integral impeller and rotor which is entirely supported by an integral combination of permanent magnets and electromagnetic bearings and rotated by an integral motor, (ii) a pump housing and arcuate passages for fluid flow and containment, (iii) a brushless driving motor embedded and integral with the pump housing, (iv) a power supply, and (v) specific electronic sensing of impeller position, velocity or acceleration using a self-sensing method and physiological control algorithm for motor speed and pump performance based upon input from the electromagnetic bearing currents and motor back emf—all fitly joined together to provide efficient, durable and low maintenance pump operation. A specially designed impeller and pump housing provide the mechanism for transport and delivery of fluid through the pump to a pump output port with reduced fluid turbulence.

These and other objects and features of the present invention will become readily apparent from the following description in which preferred and other embodiments of the invention have been set forth in conjunction with the accompanying drawings and appended claims.

BRIEF DESCRIPTION OF THE DRAWINGS

The above and other objects, features and advantages of the invention will become apparent from a consideration of the following detailed description presented in connection with the accompanying drawings in which:

FIG. 4A is a plane view of FIG. 3 taken along line A;

FIG. 4B is a cross-sectional view of FIG. 3 taken along line A;

DETAILED DESCRIPTION

Figure 1:
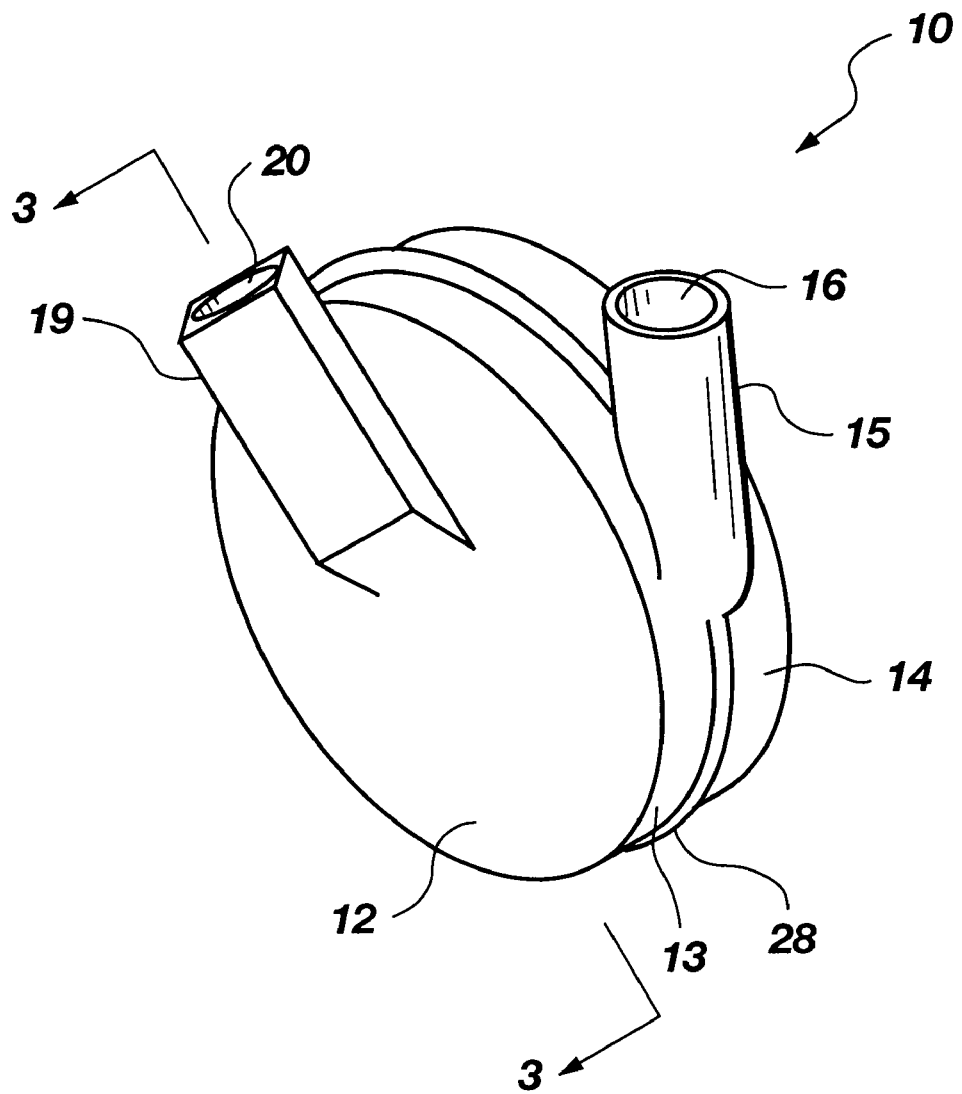
FIG. 1 is a perspective view of the magnetically supported and rotated pumping apparatus of this invention.

Reference will now be made to the drawings in which the various elements of the present invention will be given numeral designations and in which the invention will be discussed so as enable one skilled in the art to make and use the invention. It is to be understood that the following description is only exemplary of the principles of the present invention, and should not be viewed as narrowing the appended claims.

General Discussion

The underlying rationale for a rotating centrifugal pump with an impeller, fully supported by a combination of permanent magnets and electromagnetic bearings and rotated by an electric motor, is to prevent damage to blood or other sensitive fluid due to conditions of (1) excessive heat, (2) stagnation, (3) coagulation (thrombosis), or (4) high shear of fluid or blood components (hemolysis) due to fluid instability caused by turbulence or mechanical working of fluid due to harsh pump mechanism or geometry. Furthermore, the apparatus size of this invention is capable of fitting into available anatomical space if used for total natural heart replacement or ventricular assistance.

To be suitable as a blood pump, the pump must be able to adequately meet physiological perfusion needs of a ventricular or biventricular assist device for total heart replacement. As a total heart replacement device, the pump must be of sufficiently small size and mass to be implantable within available anatomical space and not cause any negative effects on surrounding organs due to excessive apparatus weight. Furthermore, the disc-like shape of the impeller of this invention significantly reduces size and complexity of the pumping apparatus. The pumping apparatus of the invention can be used singularly as a ventricular assist device that assists or replaces partial heart function or a pair of devices can be combined to form a total mechanical heart replacement. The combined size of two devices in a total mechanical heart replacement is approximately the size of a natural heart, thereby enabling implantation within existing anatomical space.

The impeller of this invention is entirely suspended and enclosed within its pump housing, thereby providing contact-free operation between pump impeller and any other portion of the pump. The pump impeller is magnetically suspended with a combination of permanent magnets and electromagnetic bearings. The permanent magnets are configured in reverse polarity which provide positive radial stiffness while being employed in the radial gaps inherent in disk-shaped impellers unlike the repulsive permanent magnet rings cited in the prior art patents which can only be employed in axial gap configurations. This reverse polarity permanent magnet configuration is required for a disk-shaped impeller geometry. It is enclosed within its pump housing, thereby providing contact-free operation between pump impeller and any other portion of the pump. The pump impeller is suspended by a combination of permanent and electromagnetic forces. An electric motor rotates the pump impeller to perform the pumping function of fluid. The notable absence of shafts, ball bearings, shaft seals or other sources of contamination make possible significantly extended product life of the pumping apparatus of this invention, thereby enabling long term natural heart replacement.

The pump impeller rotates about an axis and the term "axial direction" is employed here to denote the direction parallel to the axis of rotation of the pump impeller. The term "radial direction" is used here to denote directions perpendicular to the axial direction. The invention consists of permanent and electromagnetic bearings, comprising magnetic and other materials, activated by electrical currents in coils wound around the bearing magnetic components, which develop axial forces and provide adjustments to impeller positioning relative to pump housing. A multiplicity of magnetic bearings, in a suitable configuration arranged around the impeller, is required to center the impeller during operation of the pump and to avoid contact between the rotating and stationary components. Six impeller degrees of freedom: three translations and three rotations, must be controlled. This non-contacting operation allows the bearings to operate without wear or friction losses.

A feedback electronic controller is provided in the suspension system to automatically adjust the activating (thrust) bearing coil currents which, in turn, adjust the control forces exerted by the magnetic bearings on the rotating impeller in response to the applied forces. Such electronic controller is continuously provided with an electronic signal which is related to the position or velocity or acceleration or a combination of position, velocity and acceleration, of the rotating impeller in the available clearance space inside the pump frame during operation. Switching or direct current power amplifiers and power supplies necessary to operate the electromagnetic actuators in the magnetic bearings are provided in the invention.

Impeller position and rotational speed of this invention are controlled by specific algorithms which sense fluid pressure and the axial location of pump impeller within pump housing, correspondingly making adjustments to rotational speed and/or impeller position to provide a fully integrated system of physiological control. Impeller rotational speed is adjusted to correspond to fluid pressure at pump preload pressure (inlet pressure) and/or exit pressure to match bodily needs for increased or decreased pump flow rate or pressure rise. This also avoids excessive rpm and thus suction thereby avoiding excessive pressure.

The geometric design of the pumping apparatus of this invention provides fluid movement throughout the entire pump mechanism in a smooth, non-turbulent, and low thermal manner. Impeller rotation causes fluid to move centrifugally by specially curved impeller vanes which emanate from the epicenter of the disc-like impeller and extend toward the outside of the impeller, and simultaneously create a partial vacuum at the region near the impeller's axis of rotation that draws additional fluid into the inlet port. Blood, or other sensitive fluid, does not stagnate at any location within the pumping apparatus due to return fluid flow along the side of the impeller which returns fluid to the impeller epicenter without flow interference from stagnation pockets, bearings or seals. Importantly, the geometry of the pump housing, the impeller vanes, the outlet port, and all other aspects of the pumping apparatus of this invention are such that sensitive fluids are protected from damage otherwise caused by stagnation, excessive heat, turbulence, and excessive mechanical working of the fluid.

The fluid is transported throughout the entire pumping apparatus without harsh angular redirection to flow. The configuration of pump housing is designed with a spiral volute curve such that the same curve slope throughout the pump housing enables fluid to be transported within the pump housing with no net abrupt angular change of direction, nor corresponding net increase in thermal friction and energy loss due to friction from the pump side wall.

Another important feature of the pumping apparatus of this invention is the capability of operation in either pulsatile or non-pulsatile mode. Cyclic variance of impeller rotational speed will cause the pump to operate in a pulsatile mode, which more closely resembles pumping action by the natural heart, whereas uniform impeller rotational speed operates the pump in non-pulsatile mode. Operational mode change from pulsatile to non-pulsatile or vice versa is accomplished through changes to the pump operation settings, thereby avoiding trauma associated with replacing the total pumping apparatus when a change from either pulsatile or non-pulsatile is determined to be the preferred operation mode.

One aspect of this invention, unlike prior art devices, is that means are provided in the magnetic suspension system to generate the electronic feedback signal related to the position, velocity or acceleration of the rotating impeller either via a physical medium such as an eddy current, induction, optical, capacitance or other approach, or via a self-sensing electronic signal obtained from the current or voltage wave form, or a combination of the current and voltage wave form provided to the activating coils in the magnetic bearings. In the case of a physical sensor device placed in the pump frame near the clearance gap between the frame and the rotating impeller, the gap between the frame and the rotating impeller, the electronic position, velocity, or acceleration signal, is obtained from signal conditioning electronics. Wiring is provided for input of the signal into the electronic controller for the magnetic bearings. In the preferred embodiment, a self-sensing signal is used and the signal conditioning is provided for determining the position, velocity, or acceleration of the rotating impeller without a physical device, which allows for a minimum number of wires required in the wiring pathways between the electromagnetic actuators and the electronic controllers.

The electromagnetic bearings and their control electronics possess a physical sensor or self sensing signal such that forces (velocity, or acceleration) attempting to displace the impeller are immediately sensed and the current delivered to the coils is altered, thus avoiding impeller displacement resultant from those forces.

The flow (cardiac output) of the natural heart is primarily regulated by the venous return (preload). Another very important feature of the invention, named the physiologic controller, provides a signal which is used to determine changes in the preload or filling pressure to the pump. The controller sends a signal from monitoring changes in current flows in the thrust bearing. This information is employed to control the rotational speed of the impeller, to regulate pump suction pressure, and to regulate the needed pump outputs. This unique feature of the magnetically suspended pump allows for sensing of the inflow pressure (preload) and thus the flow (cardiac output) consistent with the physiologic needs of the recipient as a ventrical assistance device (VAD). When two pumps are used as a total artificial heart (TAH) the rotational speed of each pump will be regulated independently and each pump will be sensitive to the preload thus providing changes in flow and balance consistent with the changing physiologic needs of the recipient. This feature allows the pumps to be used without the need of the complexities associated with volume displacement chambers required with pulsatile pumps.

The invention provides for a motor to impart the necessary torque and rotation to the rotor. This is a three phase brushless DC motor controlled by using back EMF. The motor is in the shape of a disc located in the base of the housing frame and near the center of rotation of the impeller. Commutating the motor with back EMF allows effective start-up and precise control of the speed of rotation. Changes in the rotation speed are predicated on the preload as described above in the form of a physiologic controller.

Preferred Embodiments

Referring now to FIG. 1, the magnetically suspended and rotated centrifugal pumping apparatus of this invention is shown generally as construct 10. Construct 10 is configured with a first pump housing half 12 and a second pump housing half 14, together with hermetic seal 28, to form the confines for enclosure of the remainder of the pumping components, discussed in detail hereafter. The electronic controller and batteries or other power source for operation, though necessary for operation, are not shown. Construct 10 is configured with one or more pump inlet vessels, shown in FIG. 1 with one inlet vessel 19 as the preferred embodiment. Pump inlet vessel 19 is seamlessly formed and integral to first pump housing half 12 and includes an inlet throughbore 20 which provides containment for fluid entering pump construct 10. Fluid enters pump construct 10 via pump inlet vessel 19, which provides containment and delivery of fluid by inlet flow throughbore 20, to a region proximate to the axial center of pump construct 10. Outlet vessel 15 is located tangentially from the outside diameter of construct 10 and is formed by the combining of first pump housing half 12 and second pump housing half 14 with containment walls forming pump outlet throughbore 16 and sealed by hermetic seal 28.

Figure 2:
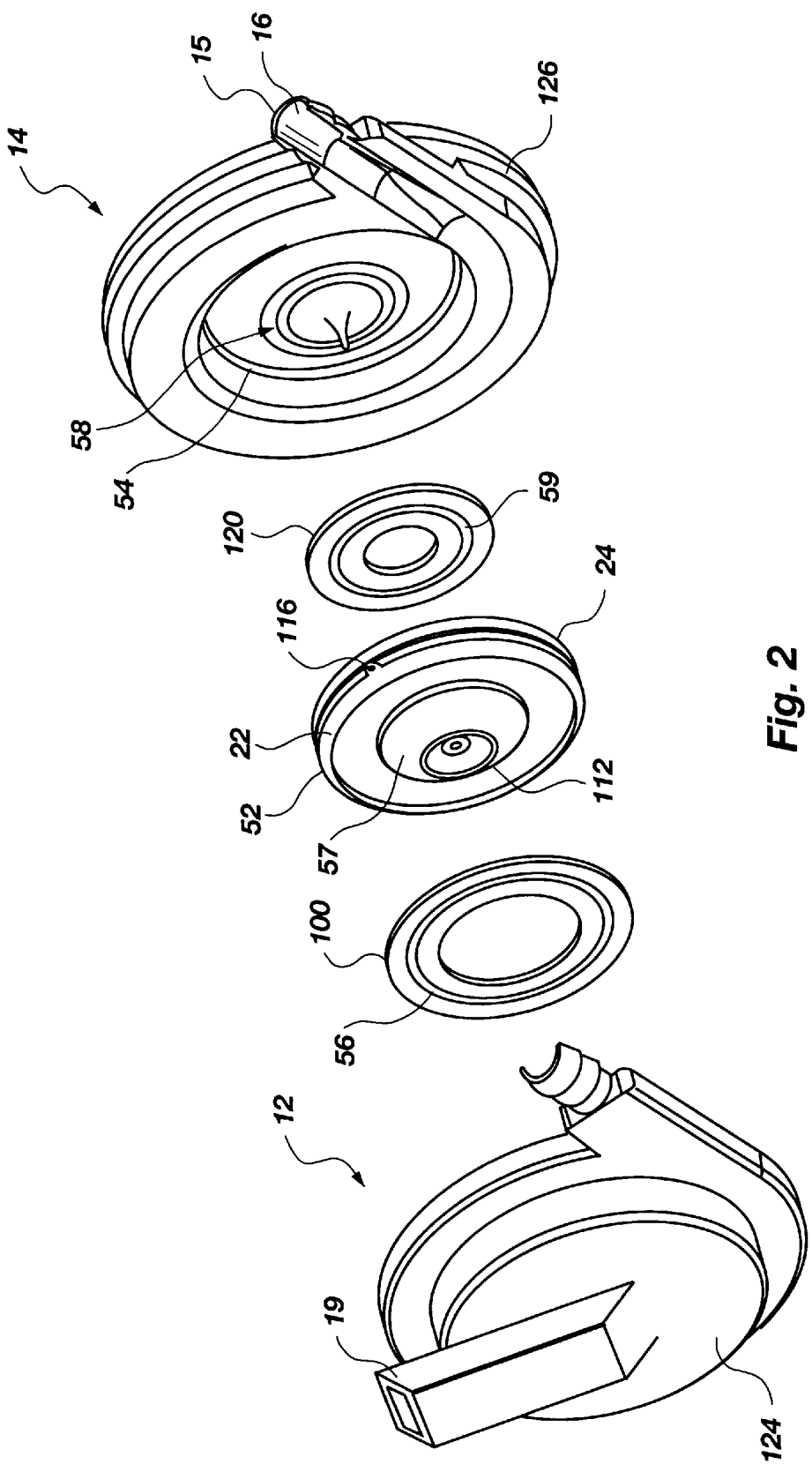
FIG. 2 illustrates an exploded side view of a pumping apparatus fully supported by one electromagnetic bearing and a plurality of permanent magnets, and rotated by an electric motor of this invention.

FIG. 2 illustrates an exploded side view of the magnetically supported and rotated pumping apparatus of this invention. The exploded view shows the pump inlet 19, the first pump half 12, a bearing target 100 having a permanent magnet set 56, an impeller shroud 22, an impeller hub 24, an impeller inlet 112, permanent magnets 52 and 57, an impeller vane 116, a motor rotor 120 having a permanent magnet set 59, permanent magnets, 54 and 58, the outlet vessel 15, and the pump outlet throughbore 16. Also shown in FIG. 2 is a combined axial thrust, moment, and radial bearing housing 124 and a combined axial thrust, moment, and radial bearing housing 126.

Figure 3:
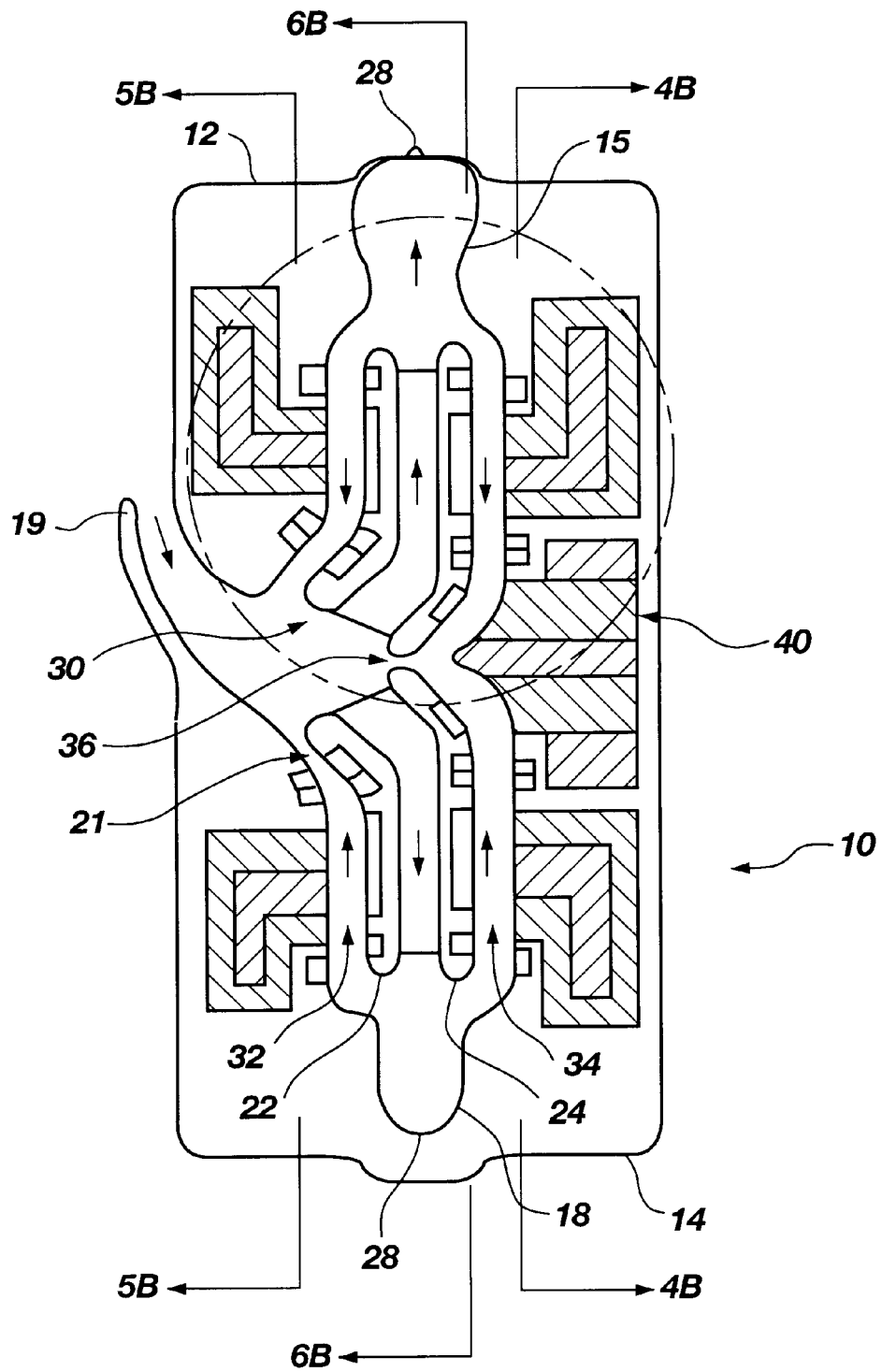
FIG. 3 is a cross-sectional view of FIG. 1 taken along line 3—3.

Referring to FIG. 3, spiral volute exit 18 is formed by the combination of first pump housing half 12 and second pump housing half 14, and sealed by hermetic seal 28. Importantly, the configuration of the logarithmic spiral volute exit 18 of this invention utilizes a spiral volute curve formation to eliminate abrupt or harsh changes of direction to fluid flow during transportation from impeller to outlet vessel 15, thereby avoiding damage to sensitive fluids as described herein before. The combination of first pump housing half 12 and second pump housing half 14, together with hermetic seal 28, also forms containment for internal impeller 21 and impeller chambers 27a, 27b, 27c, and 27d (see FIG. 9), discussed hereafter in detail. Fluid flows entirely around impeller 21 via first return flow chamber 32 and second return flow chamber 34.

FIG. 3 also shows an embodiment of a motor 40 that controls the rotational speed of the impeller 21.

FIGS. 4A and 4B depict a portion of the pump 10. FIG. 4A shows a plane view of section 4B (see FIG. 3) of the second pump housing half 14 and FIG. 4B shows a side view of section 4B of FIG. 3. Windings (or control coils) 52 and a bias coil 53 are shown that enable construction of the pump 10 by those skilled in the art. Axial thrust bearing function which is controlled by an electronic controller.

Figure 5A:
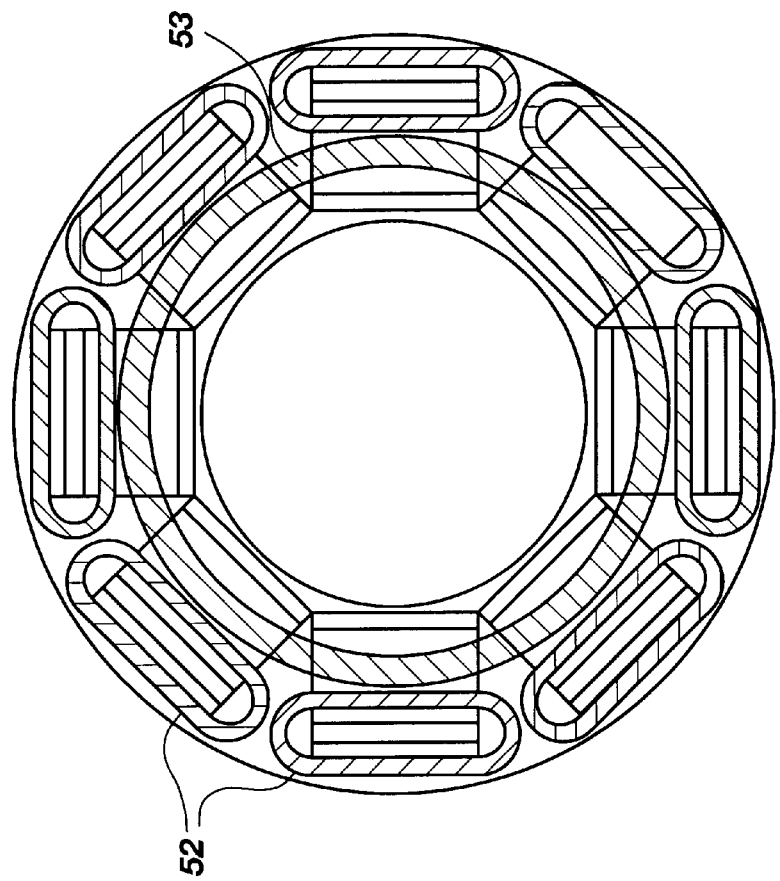
FIG. 5A is a plane view of FIG. 3 taken along line B.
Figure 5B:
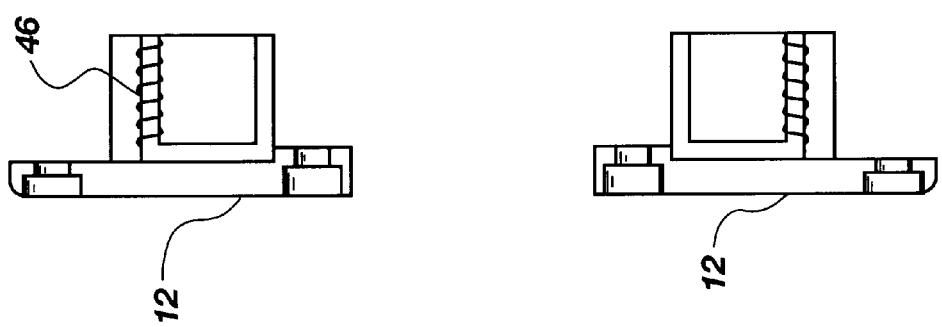
FIG. 5B is a cross-sectional view of FIG. 3 taken along line B.

FIGS. 5A and 5B depict another portion of the pump 10, however, FIG. 5A shows a plane view of section 5B (see FIG. 3) of the first pump housing half 12 and FIG. SB shows a side view of section 5B of FIG. 3. Once again, windings (or control coils) 52 and a bias coil 53 are shown that enable construction of the pump 10 by those skilled in the art. This combination performs an axial thrust bearing function which is controlled by an electronic controller.

Figure 6B:
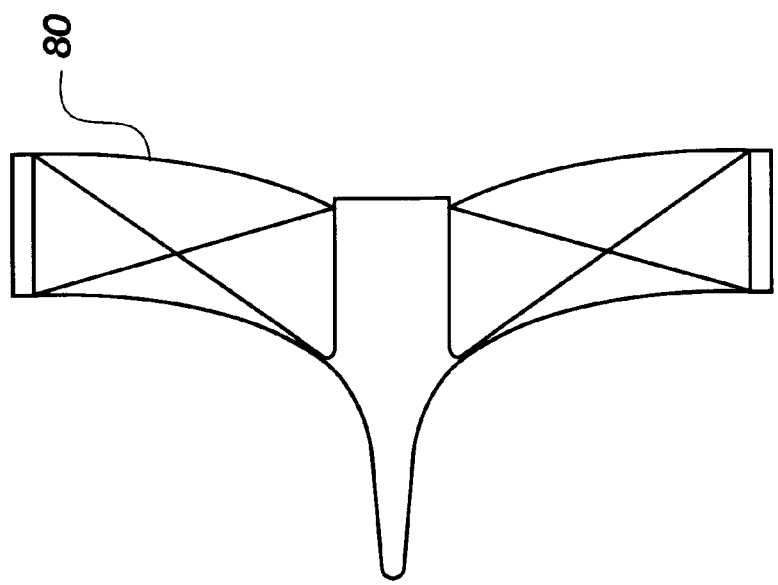
FIG. 6B is a cross-sectional view of FIG. 3 showing a preferred embodiment of a motor stator.
Figure 6A:
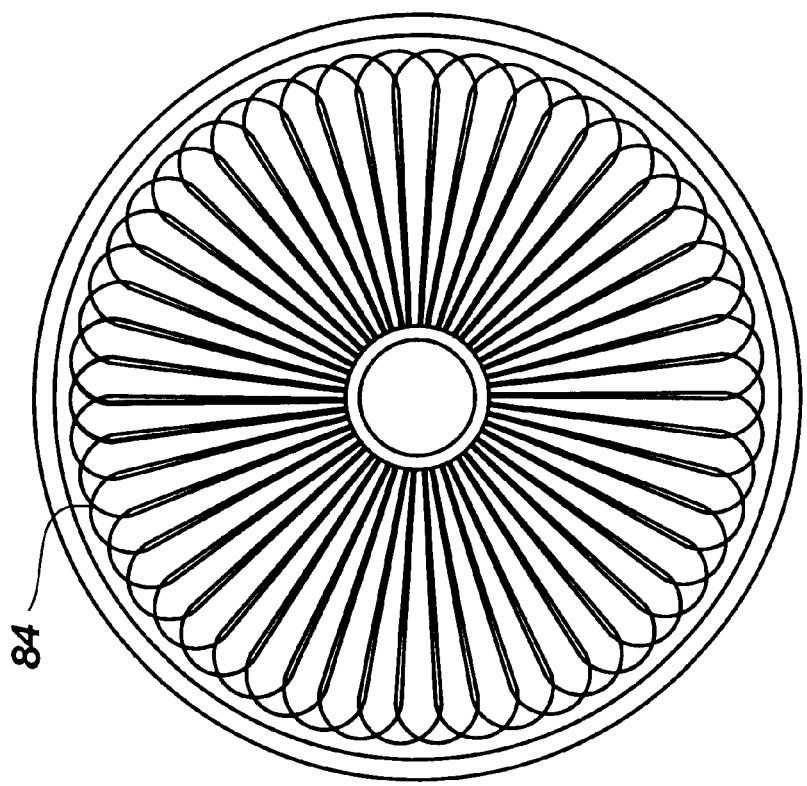
FIG. 6A is a plane view of a preferred embodiment of FIG. 3 taken along line C.

FIGS. 6A depicts section 6B of FIG. 3 in plane view to demonstrate the windings 84, and FIG. 6B shows a preferred embodiment of the stator 80 of the motor 40. The motor 40 will be described in greater detail hereinafter.

Figure 7A:
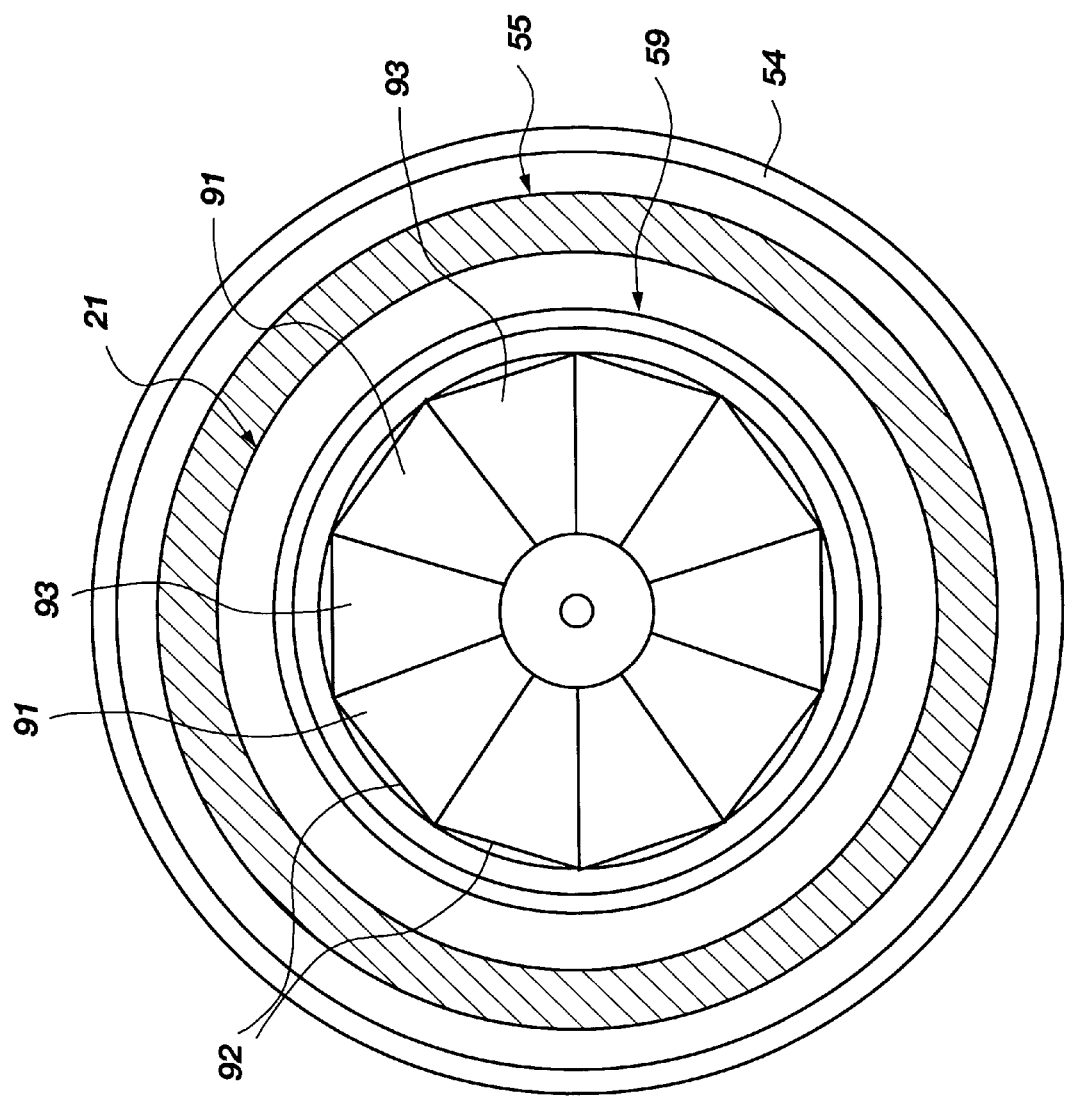
FIG. 7A is a plane view of FIG. 3 taken along line C.

FIG. 7A depicts section 6B of FIG. 3 in plane view to show the rotor or impeller 21 portion of the motor 40 and to demonstrate the arrangement of the permanent magnets 92 on the rotor. The magnets 92 are arcuately arranged and alternate north pole 91, south pole 93, north pole 91, south pole 93, etc. until the circular arrangement depicted in FIG. 7A is accomplished.

Figure 7B:
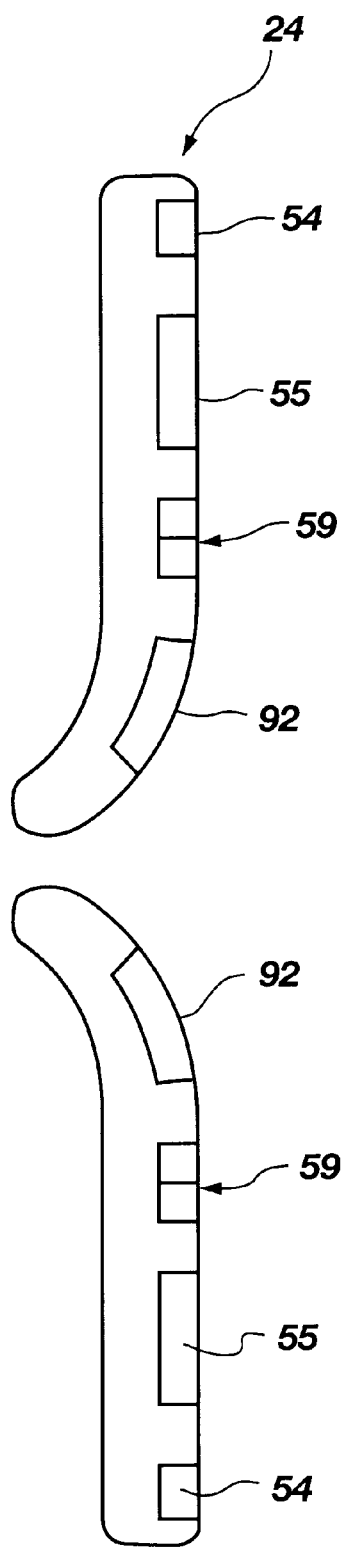
FIG. 7B is a side view of a portion of the impeller in FIG. 3.

FIG. 7B shows the same portion of the impeller (or rotor) 21 in cross-section. Also shown in both FIG. 7A and 7B is the permanent magnet ring 54, the permanent magnetic ring set 59, and magnetic material 55 that is the target of the axial thrust bearing. The rotor 21 will be described in greater detail hereinafter.

Figure 8:
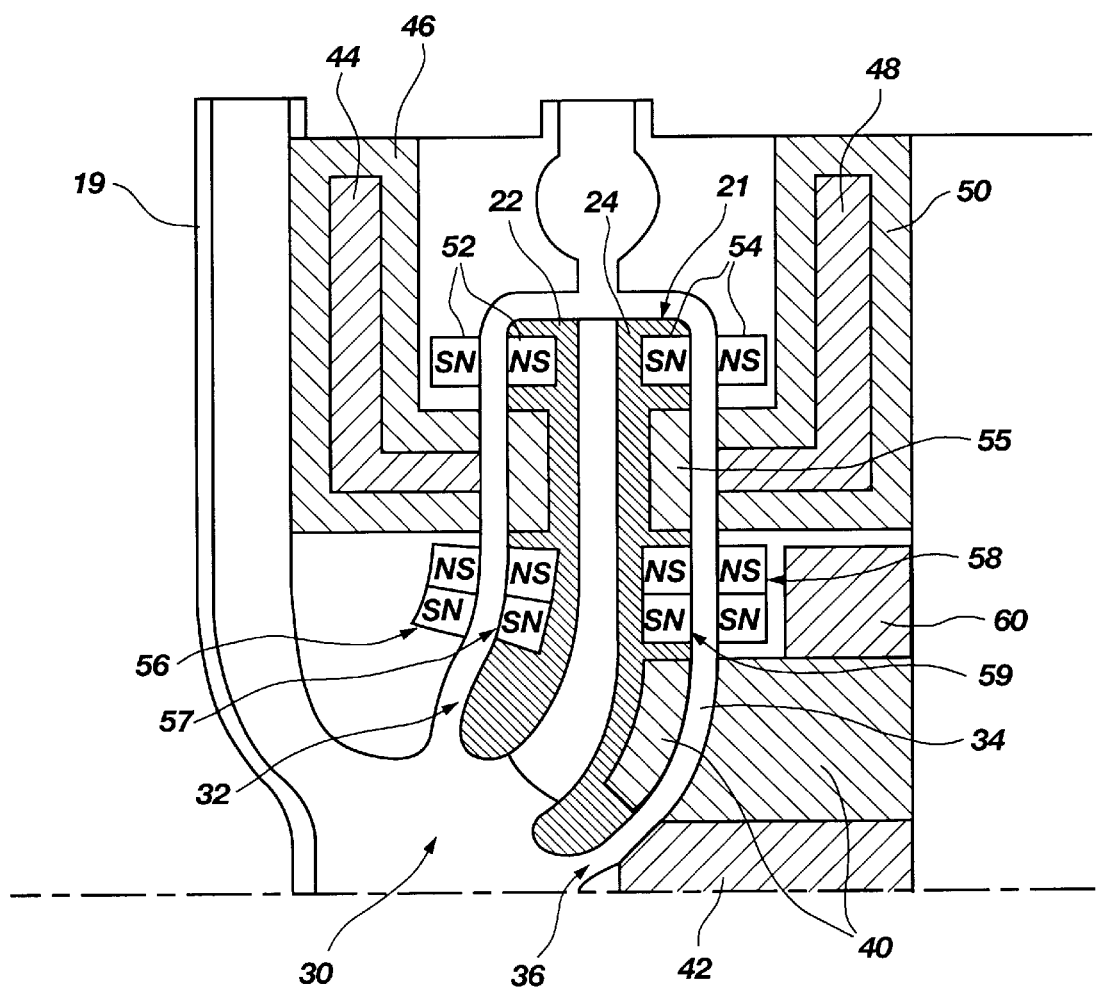
FIG. 8 is an enlarged, fragmentary, cross-sectional view of the pump impeller and housing of FIG. 1.

FIG. 8 is an enlarged, fragmentary cross-sectional view of the pump impeller and housing of FIG. 1. FIG. 8 focuses on a portion of the cross-section view shown in FIG. 3 and provides greater clarity to the disclosure discussed relative to FIG. 3.

Figure 9:
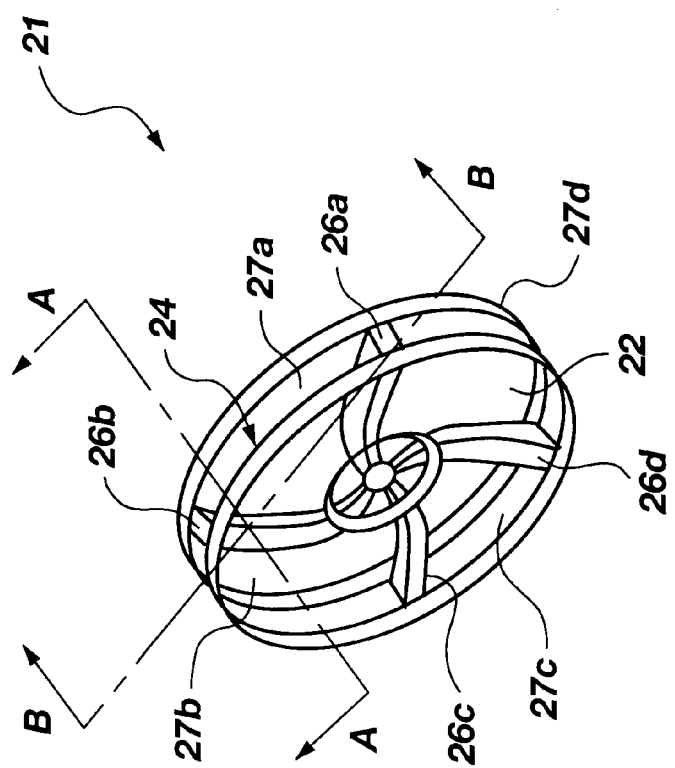
FIG. 9 is a perspective view of the pump impeller of this invention shown in semi-transparent mode for clarity.

Pump impeller 21 is configured with two or more impeller vanes 26a, 26b, 26c, and 26d, shown in FIG. 9, with a preferred embodiment of four impeller vanes 26a, 26b, 26c and 26d. Each impeller vane 26 is mounted between impeller shroud 22 and impeller hub 24 such that impeller chambers 27a, 27b, 27c and 27d are formed. Each impeller vane 26a, 26b, 26c, and 26d corresponds to impeller chambers 27a, 27b, 27c, and 27d respectively.

Figure 10:
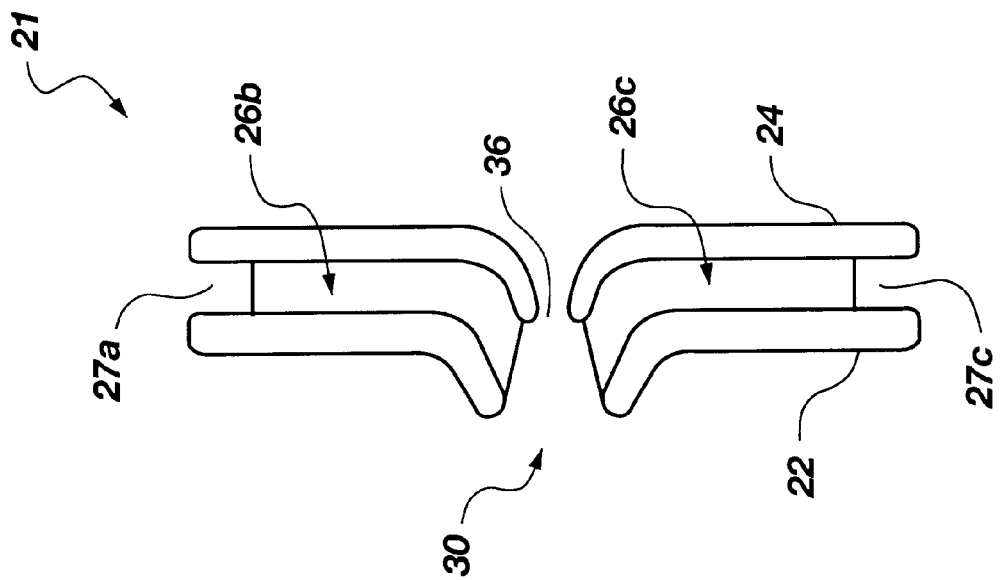
FIG. 10 is a cross-sectional view of the pump impeller taken along lines A—A of FIG. 9.
Figure 11:
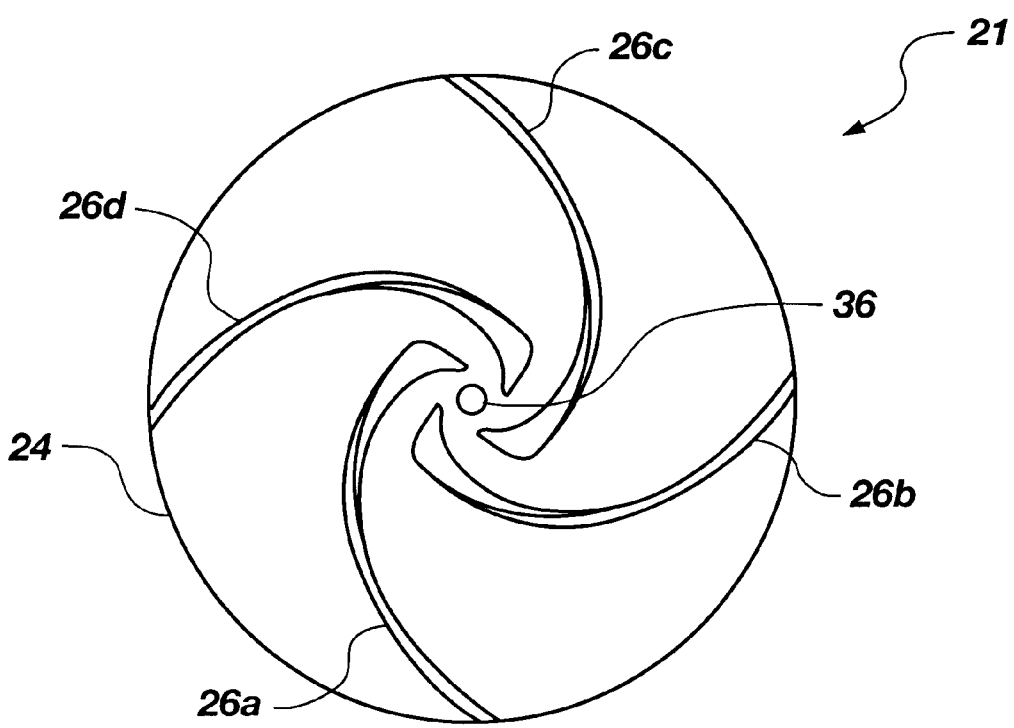
FIG. 11 is a front view of the pump impeller, taken along lines B-B of FIG. 9, with shroud assembly removed.

Referring to FIGS. 9, 10, and 11, impeller vanes 26 are configured with a spiral curvature such that rotation of impeller 21 brings impeller vanes 26 in contact with fluid to be pumped, thereby causing fluid to move radially toward spiral volute exit 18. Rotation of impeller 21 centrifugally transports fluid from the region at the axial center of construct 10 toward the spiral volute exit 18, correspondingly creating a partial vacuum at the region of impeller intake opening 30 and drawing in additional fluid through intake vessel 19 (FIG. 1). Specifically, as shown in FIG. 11, the impeller is designed to allow for a smooth transition of the flow vector from inlet to outlet. This is accomplished in one particular embodiment employing a blade angle of 17° at the base of the blade at the inlet, A. The blade angle is gradually decreased to 11° at the top of the blade at the inlet, B. Hence the blade is not straight in the axial direction near the inlet. The blade gradually transitions to being straight in the axial direction with an angle of 37° near the midpoint of the blade, C. This 37° angle is maintained to the exit point, D. All blade angles are the inner angles of the blade relative to a tangent to a circle centered in the center of impeller 21. Referring to FIG. 2, the pump volute is located in pump stationary component to provide a smooth flow of pumped fluid from the discharge of the impeller at relatively high velocity into the pump exit passage where it is slowed down prior to exiting from the pump. The volute increases the fluid pressure (head) by converting fluid kinetic energy (velocity) to potential energy (pressure or head).

The clearance around the impeller 21 in one particular embodiment is maintained at 0.030" to allow for good washing of the surfaces. Any changes in direction of the flow in the clearance passages are made by maximizing the radius of curvature in order to keep the flow laminar.

Referring again to FIGS. 3 and 8, in one embodiment, a portion of fluid pumped by impeller 21 returns from the region of high pressure near spiral volute 18 along both sides of impeller 21, via first impeller return chamber 32 and second impeller return chamber 34, as reverse flow to region of lower pressure near impeller intake opening 30. Fluid returning along second impeller return chamber 34 also passes through impeller return opening 36, and thereby serves to equalize internal pressure. The width of impeller return chambers 32 and 34 are calculated by a precise balance of primary fluid flow and reverse flow, such that fluid does not stagnate within the pump but also does not possess unnecessary inefficiencies.

Pump impeller 21 is suspended within its pump housing by permanent magnet sets 52, 54, 56, 57, 58, and 59 in combination electromagnets 44, 46 and 48, 50. Permanent magnet set 52 is a magnetic ring located at the practical circumference edge of impeller shroud 22 and is oriented with north poles proximal and south poles distal thereby utilizing the magnetic repulsive forces away from interior wall of first pump half 12. Correspondingly, permanent magnet set 54 is it magnetic ring located at the practical circumference edge of impeller hub 24, and is oriented with north poles proximal and south poles distal thereby utilizing magnetic repulsive force away for interior wall of second pump housing 14, but whose direction of force opposes permanent magnet set 52, such that impeller 21 is stabilized axially at the circumference of impeller 21.

First housing permanent magnet set 56 and first impeller permanent magnet set 57 are configured in a double ring configuration located proximal to impeller intake opening 30, with alignment on either side of first return flow chamber 32, and are integral to first pump housing half 12 and impeller shroud 22, respectively. The reverse polarity of first housing permanent magnet set 56 and first impeller permanent magnet set 57 for each of the two magnetic rings, enables radial stabilization and, due to the angular positioning, also provides a degree of translational stabilization of impeller 21.

Second housing permanent magnet set 58 and second impeller permanent magnet set 59 are configured likewise in a double ring configuration and are proximal to return opening 36, with alignment on either side of second return flow chamber 34, and are integral to second pump housing half 14 and impeller shroud 24, respectively. The reverse polarity of second housing permanent magnet set 58 and second impeller permanent magnet set 59 enables radial stabilization of impeller 21 and a degree of translational stabilization of impeller 21.

The double ring configuration of the magnetic sets is a double magnet reverse polarity design. The magnetic sets 56, 57, 58, and 59 are each located at approximately one-half the radial point of the impeller 21. The rings of each set are placed in an attractive orientation next to one another and the sets are placed in a reverse polarity from one another. Thus, the magnetic arrangement has the property of producing positive radial stiffness. If a fluid or other force tends to push the impeller 21 off center, the attractive forces between the NS and SN rings apply a radially centering force to prevent it. For the geometry and magnetic strength described herein, the radial stiffness is approximately 67,000 N/m. The two bearing sets have a combined radial stiffness of 134,000 N/m. This double ring arrangement has been shown to keep the impeller properly centered and operating during ventricular assist duty.

It is important to note that the four sets of permanent magnet rings 56, 57, 58 and 59, as described above, provide a significant portion of the total suspension and stabilization of impeller 21 within pump housing half 12 with final stabilization, fine positioning and rotation of impeller 21 provided by electromagnetic thrust bearings 46 and 50, electric activation coils 44 and 48 and motor 40 with associated coils at 42 and 60. The magnetic suspension and rotation of impeller 21 provides a contact-free operation which increases overall product life and reliability and avoids sensitive fluid damage as discussed hereinbefore. The four magnetic rings as described above, each with reversed North and South magnetic polarities, are configured such that interacting magnetic fields produce positive radial and axial stiffness, which are necessary to counter radial and axial applied forces due to fluid, motor forces, gravitational load, acceleration forces, and other incidental forces.

Electromagnetic thrust bearings 46 and 50 are comprised of stationary magnetic actuator components, electric activation coils 44 and 48, electronic controllers (not shown), power amplifiers (not shown), a means of sensing impeller 21 position, velocity or acceleration (not shown). In summary, the respective actuators which are individually controlled enable control of the identified six axes.

An electronic controller (not shown) provides automatic adjustment to electrical current in electric activation coils 44 and 48, which change in electrical current adjusts the control forces exerted by electromagnetic thrust bearings 46 and 50. The electronic controller continuously provides electric signal input which relates to position, velocity and/or acceleration of the rotating impeller 21. Additional components necessary for operation of construct 10 are switching or direct current power amplifiers and power supplies (not shown).

As stated above, FIGS. 6A and 6B show a plane view and a cross-section view of a motor stator 80 of the motor 40. Motor 40 is a 3-phase brushless motor and provides electromagnetic force to start and rotate the pump impeller or rotor 21 including an arcuately shaped rotor disk suspended with single sided flux gap. As shown in the embodiment of FIGS. 7A and 7B, the motor 40 consists of a permanent magnet rotor 21 with permanent magnets 92 imbedded in the hub of a centrifugal or mixed flow pump. The magnets 92 are wedge shaped and arranged to form a circular rotor. The magnets 92 are arranged such that magnetization of the permanent magnets alternate north and south polarities both radially and angularly around the rotor 21. Referring to FIGS. 6A and 6B, the motor stator 80 has wire windings 84 excited by current from an electronic controller. This stator arrangement produces a magnetic field interacting with the permanent magnets 92 to produce a torque on the rotor 21.

Although the motor stator 80 can be suspended in at least three configurations depending on torque, speed, and bearing requirements, the configuration of FIG. 6A and 6B shows an ironless configuration for the motor stator; stator 80 has no saturable magnetic material. As shown in FIG. 6B, wire 84 is wound on a separate fixture and fixed in place on rotor 80 using epoxy or similar material.

The above configuration meets the unique criteria for a centrifugal or mixed flow medical device pump that is needed as was discussed in the background section. The use of permanent magnets in the rotor results in no mechanical contact between the rotor and stator of the motor. The electromagnetic bearing sets 52, 54, 56, 57, 58 and 59 allow the rotor/impeller 21 to rotate with complete lack of contact with the stator 80. The geometry of the motor meets the requirements of allowing the motor to drive the pump in an efficient manner while providing for laminar flow in the gaps between the impeller and housing, with minimal stagnation of blood. This is realized by keeping bending radii large.

Figure 12:
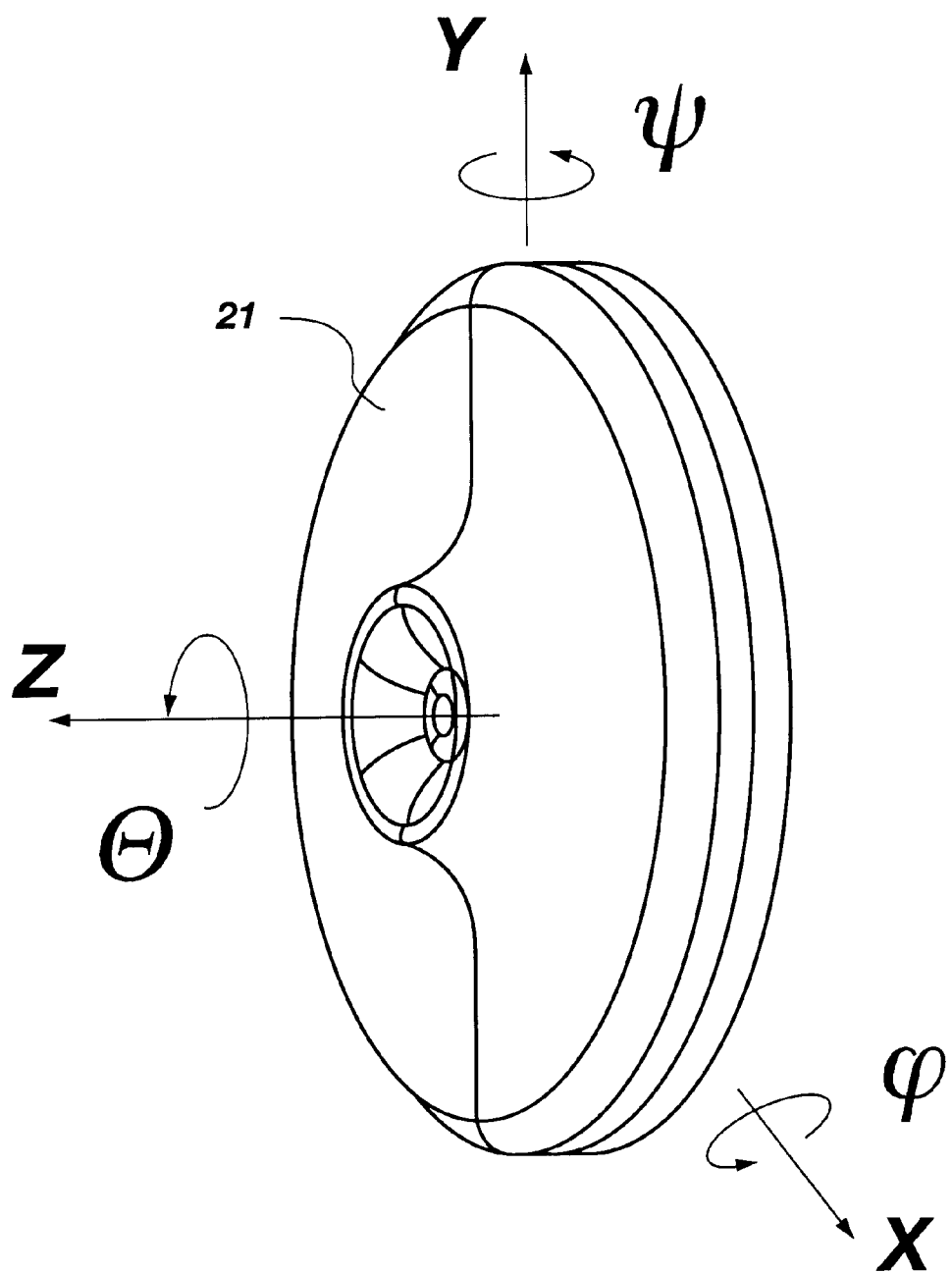
FIG. 12 illustrates the coordinate system and the symbols for the six directions of magnetic actuation for the pump of the present invention.

FIG. 12 shows the coordinate system for defining impeller 21 magnetic actuation in the required six directions: three translations (x,y,z) and three rotations ($\Phi$, $\psi$, $\theta$). All three translational displacements (x,y,z) and two rotations (pitching motions about two axes) ($\Phi$, $\psi$) are held nearly fixed in space relative to the stator by the magnetic forces. The last rotation actuation ($\theta$), about the z axis rotation, is accomplished by the motor. In summary, FIG. 13 discloses six axes of control, including (i) one axial translational axis, (ii) two radial translational axes, and (iii) three rotational axes comprising two axes controlled for moment and one axis controlled by motor rotation.

In a preferred embodiment, the magnetic bearings are constructed in two parts: 1) a thrust/moment configuration and a 2) radial/thrust configuration. Although numerous arrangements could be used to form a four quadrant actuator, in this embodiment, unlike an all electromagnetic embodiment, permanent magnets are used with the activation coils and are placed in pairs so that there are four quadrants of control. This provides a combination of axial actuation (z) and pitching moments ($\Phi$, $\psi$) The thrust force (z) is generated so that each magnetic pole in the arrangement exerts the same force on the target. The pitching angular actuation forces (moments) are also produced by the permanent magnets above and below the impeller centerline ($\Phi$ angular displacement) and to the left and right of the impeller ($\psi$ angular displacement). The function of the electronic controller is to determine what combination of currents must be employed to fine tune these axes, i.e., provide final stabilization and fine positioning and rotation. The axial thrust bearings are the only electronically controlled bearings in this embodiment of the invention.

Second, this magnetic bearing configuration can exert control forces in the axial direction (z), radial directions (x,y), and angular displacements ($\Phi$, $\psi$). These two magnetic bearing configurations, the thrust/moment and the radial/thrust configurations, produce the necessary magnetic forces and moments required to keep the impeller centered and under control.

Figure 13A:
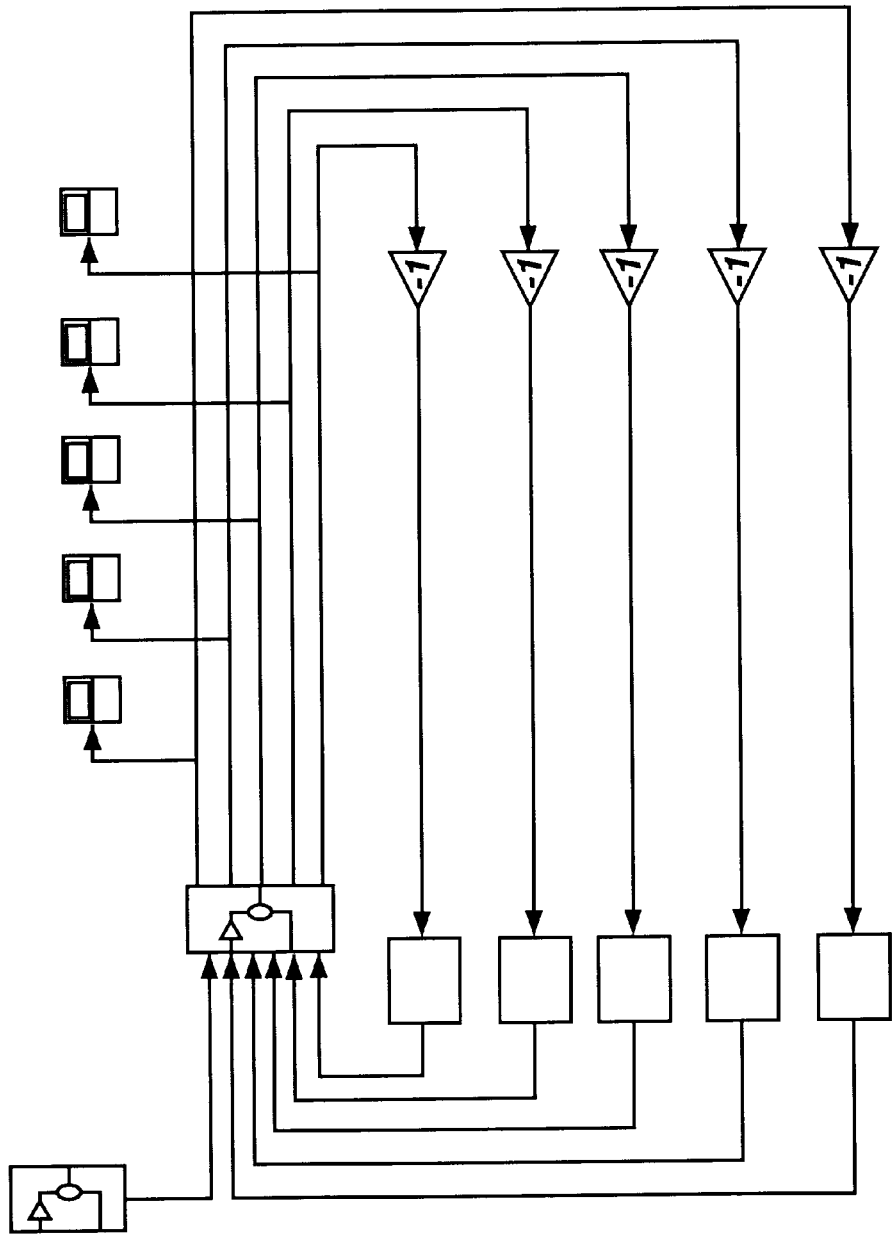
FIG. 13A shows electronic circuits that provide electronic feedback for control of the impeller position within the stator clearance region.
Figure 13B:
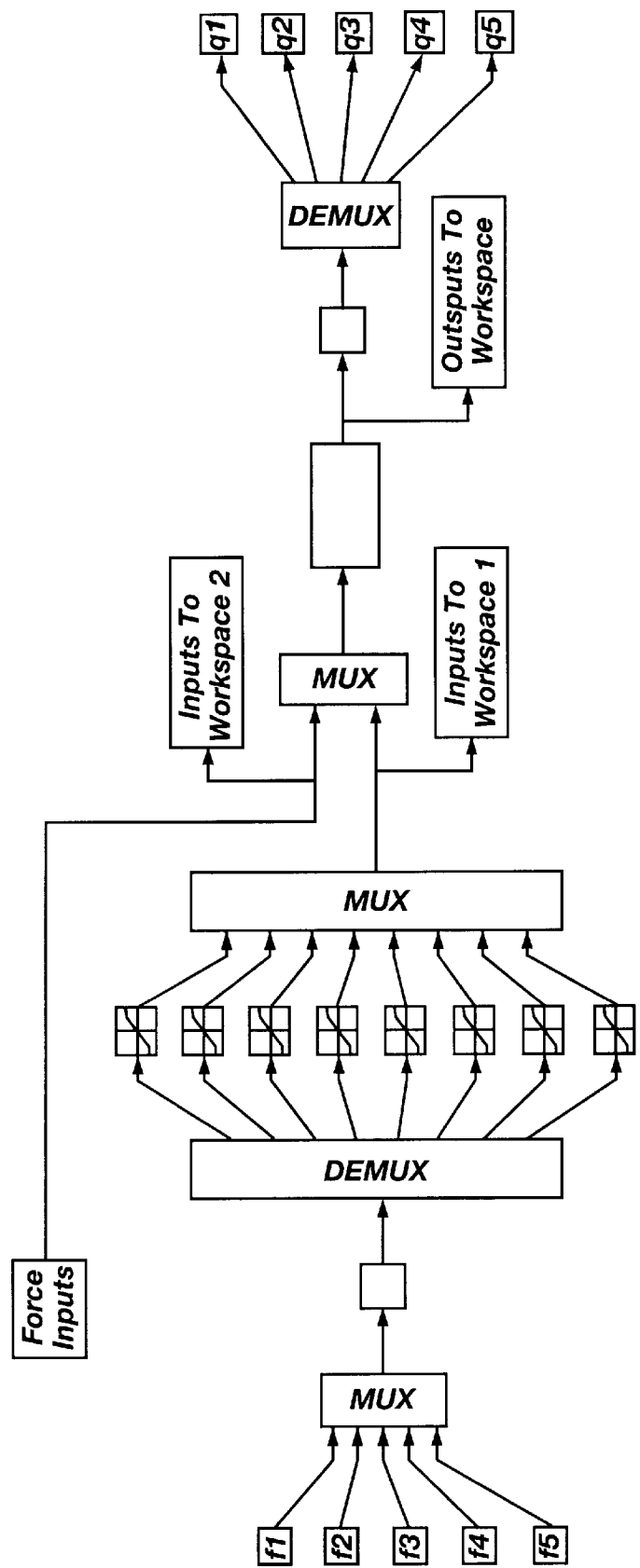
FIG. 13B shows further details of the electronic circuits of FIG. 13B that provide electronic feedback for control of the impeller position within the stator clearance region.

FIGS. 13A and 13B show an embodiment of the electronic circuits for electronic feedback control of the impeller position within the stator clearance region. In the preferred embodiment, these electronic circuits apply to the axial thrust bearing only because the axial thrust bearing is the only set of coils electronically controlled. Electronic circuits composed of resistors, capacitors, amplifiers, etc. are combined to control the impeller dynamics using proportional-integral-derivative control methods or other linear control algorithms such as state space, mu synthesis, linear parameter varying control, and nonlinear control algorithms such as sliding mode control. Particular control algorithms are used to take into account impeller rigid body gyroscopic forces, fluid stiffness, damping and inertia properties whose magnitude depend upon impeller position, rotational rate, pressure rise, and flow rate. In one embodiment, the physical circuits are miniaturized using surface mount technology, very large scale integrated (VLSI) circuit design and other means.

In the embodiment shown here, the control algorithm produces the eight coil currents which control the three displacements (x,y,z) and two angular displacements ($\Phi$, $\psi$) The controller algorithm design is robust to account for uncertainties in forces acting on the impeller such as fluid stiffness, damping and inertia properties, gyroscopic effects, magnetic forces, etc. The control algorithms are implemented on a dedicated microprocessor with adjustable parametric variation implementation to account for different physiological needs for the different applications to different size humans, from children to large adults.

Power amplifiers are employed in the invention to produce the desired coil currents for the electromagnetic bearings as determined by the electronic controller output voltage. One embodiment of a switching amplifier, operating with voltage switched either on or off at a frequency much higher than the rotational frequency of the pump impeller, is utilized in the device because power amplifiers are very efficient, having an efficiency in the range of 85 to 99%. The electronic power circuits are composed of magnetic coils, with associated resistance and inductance, resistors, capacitors, semiconductor components. The coils are implemented using wire with low resistance.

These power circuits are designed to be regenerative—that is, the magnetic bearing enabling power moves back and forth between the magnetic coil inductors to the capacitors with the only losses occurring due to the low coil resistance (ohmic losses). The high power present in the magnetic coil circuits is a small fraction of the nominal power capability; the nominal power capability being defined as supply voltage times average switched current in the coils. With these low power switching amplifiers and regenerative coil power circuits, the undesirable heating of the blood is kept to a minimum.

The invention is designed to generate the electronic signal related to the position, velocity or acceleration of the rotating impeller through one of the following: (i) a physical device such as an eddy current, induction, optical, capacitance or other approach; or (ii) a combination of the current and voltage waveform provided to the activating coils in the magnetic bearings. In the case of a physical sensor device placed in the pump frame near the clearance gap between the frame and the rotating impeller, the electronic position, velocity, or acceleration signal, is obtained from signal conditioning electronics and wiring provided for input of the signal into the electronic controller for the magnetic bearings.

In the case of a self-sensing signal, the signal conditioning is provided for determining the position, velocity, or acceleration of the rotating impeller without a physical device, which allows for a minimum number of wires required in the wiring pathways between the electromagnetic actuators and the electronic controllers.

Figure 15:
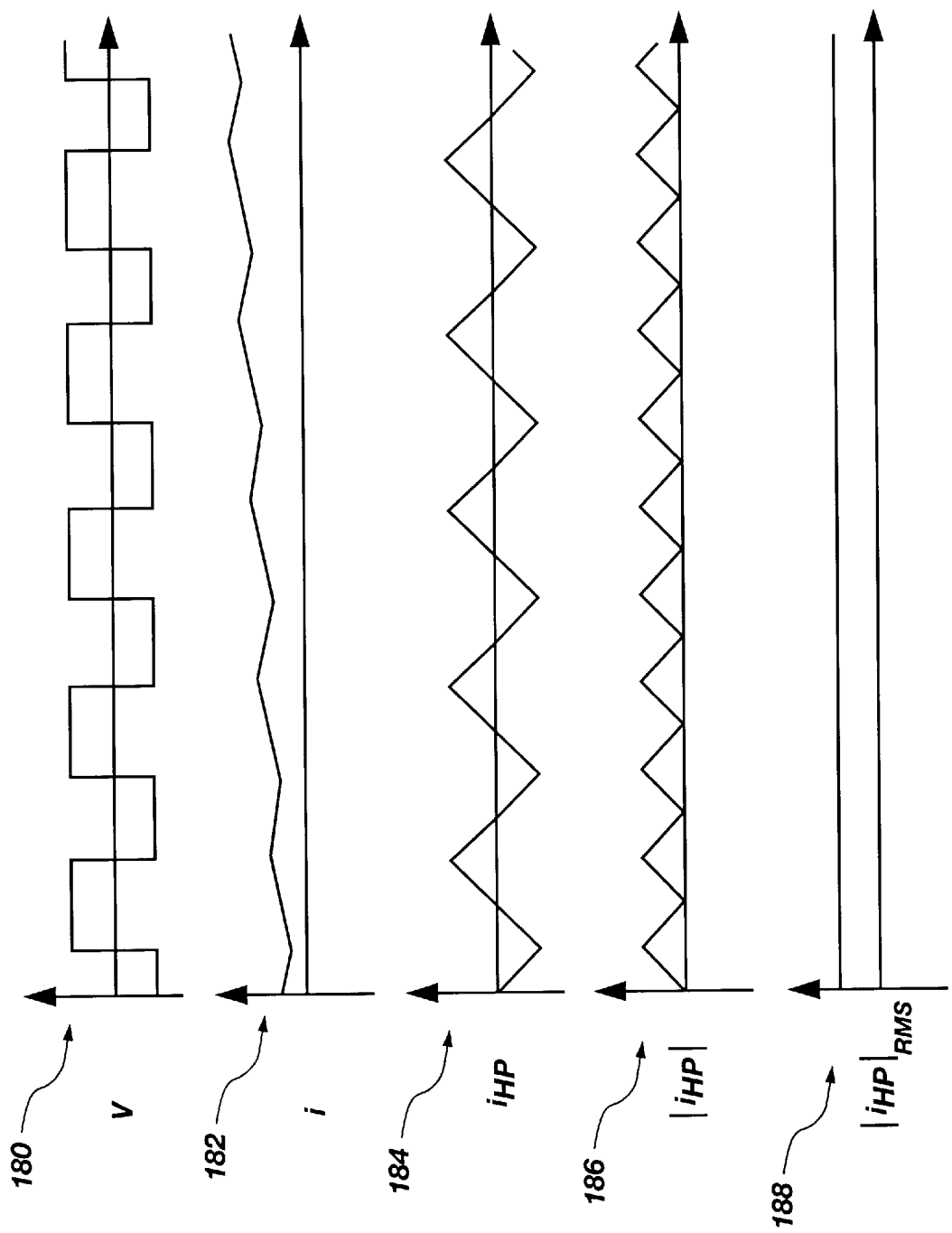
FIG. 15 illustrates a table of graphs of the signals as they pass through the filters of FIG. 14.
Figure 16:
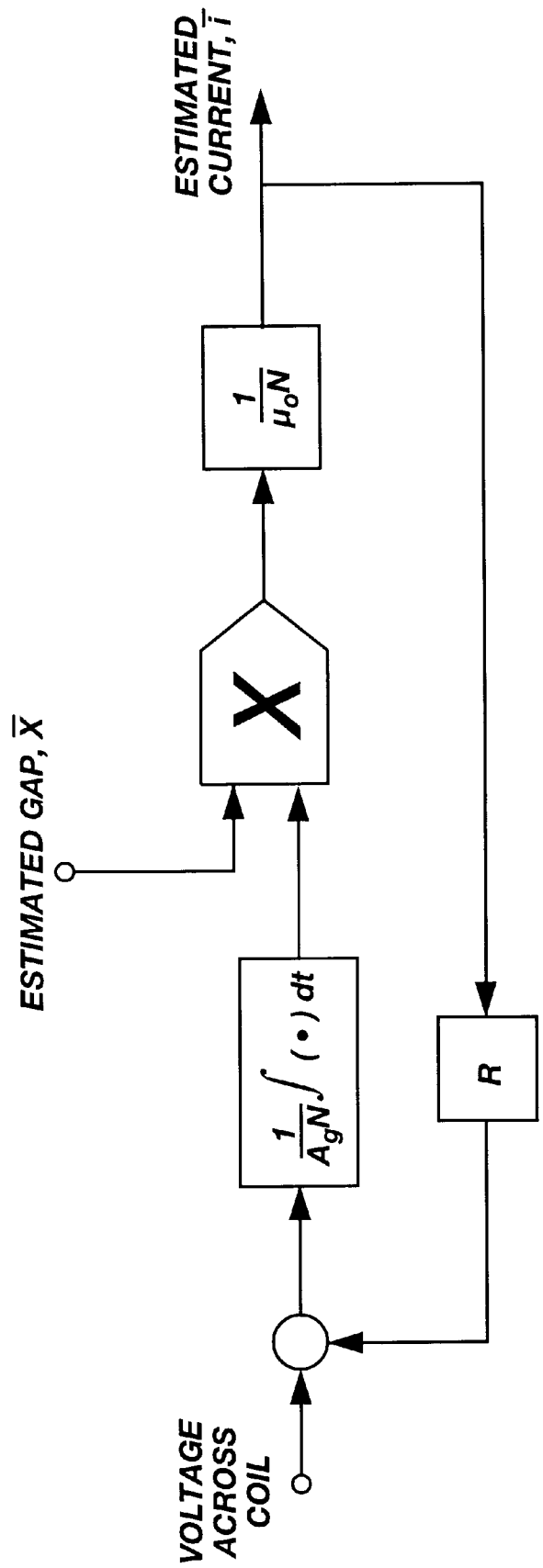
FIG. 16 depicts a schematic diagram of an integrator circuit whose gain is controlled by an analog multiplier indexed to the estimated gap.
Figure 17:
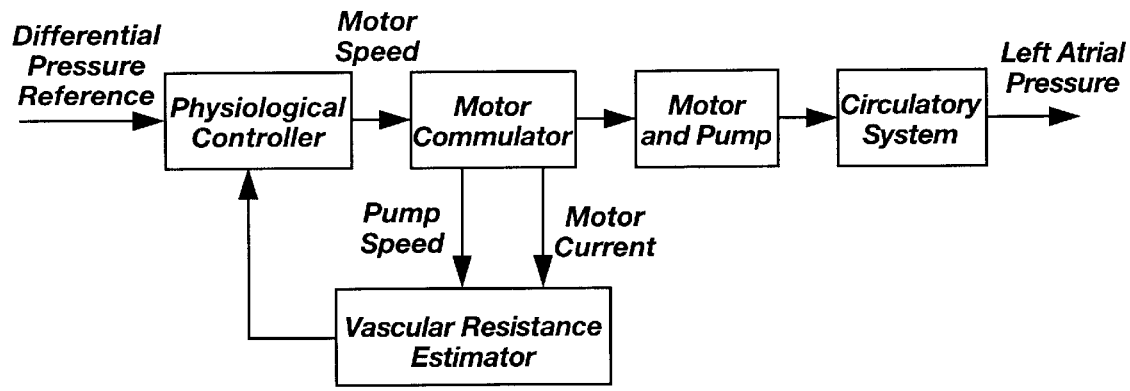
FIG. 17 shows a schematic diagram of a physiological electronic feedback control circuit based on motor current and speed.

A preferred embodiment of the sensing function of the invention is the self sensing configuration. The self sensing configuration avoids the use of a physical sensor in the stator, minimizes the size of the pump, and minimizes the number of wires required for operation. In one embodiment illustrated in FIGS. 13A and 13B, position sensing is accomplished by examining the voltage and current switching wave forms (employed with the switching power amplifiers described above for several of the electromagnetic coils. Each coil is driven by a switching power amplifier with a high (in the kHz range) carrier frequency. The resulting current waveform, one version which is shown in FIG. 15, is a combination of the relatively low frequency commanded waveform (to produce the necessary control force for positioning the impeller) and a high frequency triangular waveform due to the high frequency carrier. The amplitude (magnitude) of this commanded waveform is a function of the circuit inductance (a combined inductance due to the magnetic material properties in the magnetic bearing and due to the fluid gap), the switching frequency, the power supply voltage, and the duty cycle of the switching amplifier (ratio of on to off voltage employed in amplifier to produce the desired control forces).

Figure 14:
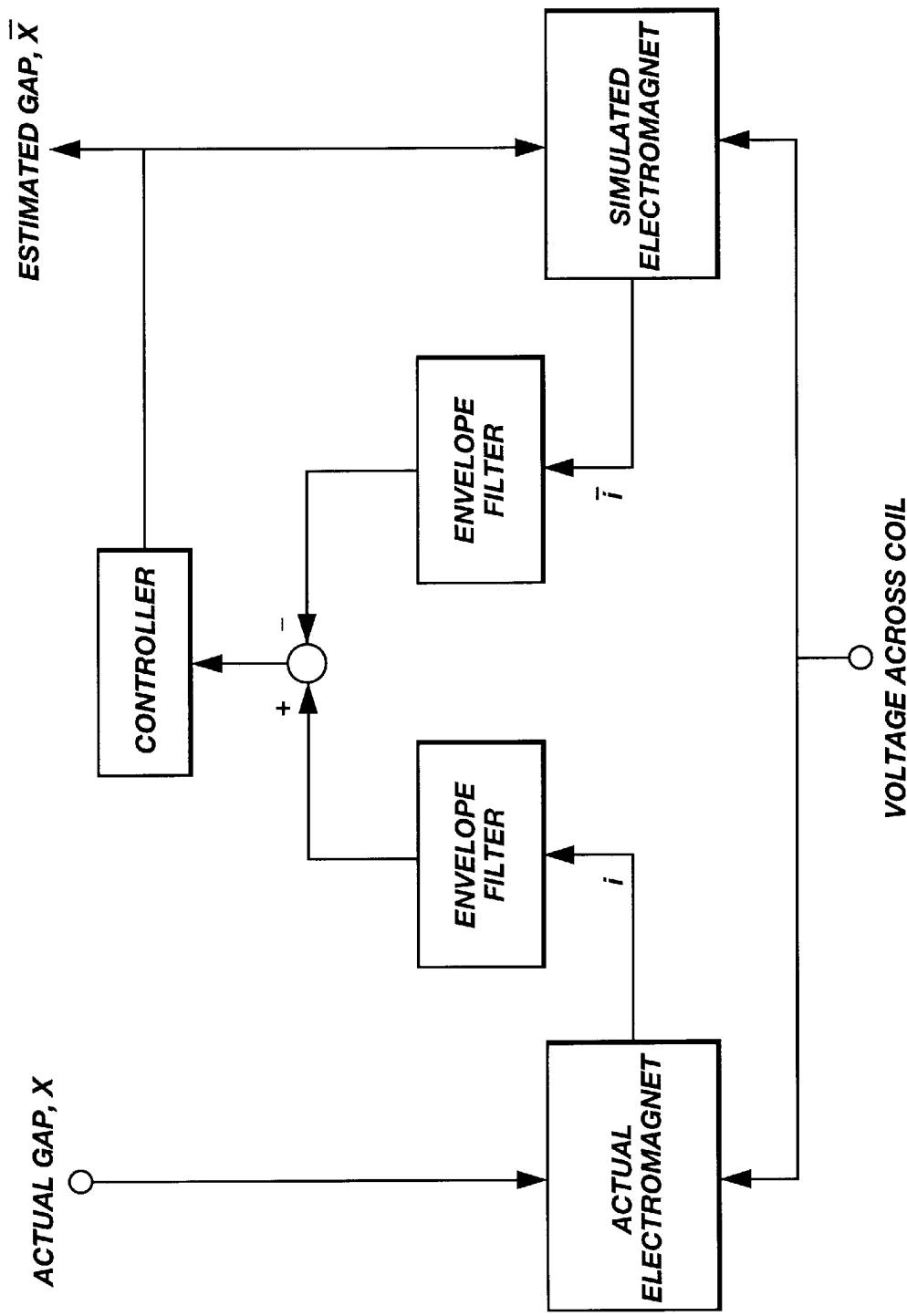
FIG. 14 illustrates electronic filters from a self sensing part of the invention, the filters extracting fluid gap dimension information while removing the effects of power supply voltage, switching frequency, duty cycle variation, and electronic or magnetic noise.

FIG. 14 shows an embodiment of electronic filters that are provided in the self sensing part of the invention to extract the fluid gap dimension information while removing the effects of power supply voltage, switching frequency, duty cycle variation, and electronic or magnetic noise. A parameter estimation method is employed to demodulate the signal and determine the fluid gap dimension. One embodiment of the envelope of filters is employed, consisting of a high pass filter to remove the bias current, a precision rectifier to make the waveform strictly positive, and a low pass filter to remove the variation in the remaining signal. The embodiments shown in FIG. 14 gives a low noise sensor with a high bandwidth, suitable for the self sensing signal determination of the fluid gap dimension.

Figure 18:
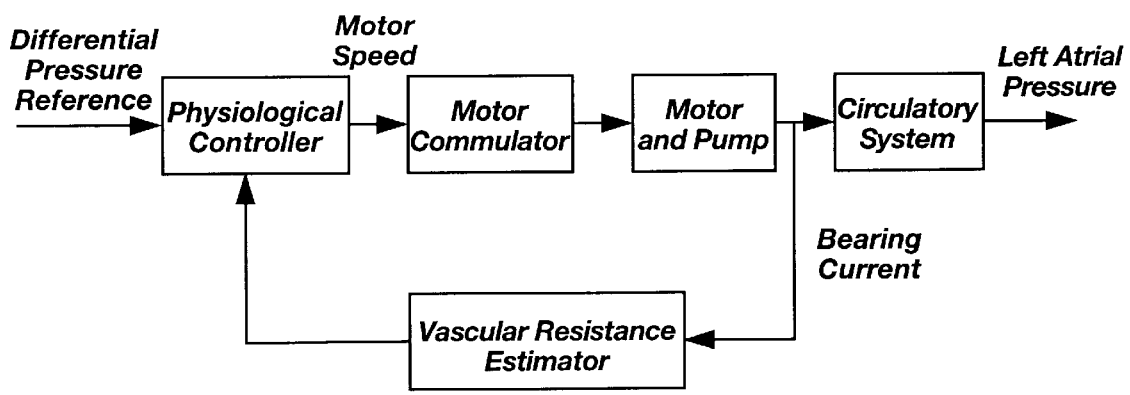
FIG. 18 shows a schematic diagram of a physiological electronic feedback control circuit based on bearing current.

FIG. 18 shows the sequence of signal forms as they pass through the filters: the graph at 180 shows the supply coil voltage, the graph at 182 shows a typical actual coil current waveform, the graph at 184 shows the current signal output from the integrator (described in detail in FIG. 19) which removes the change in coil current due to the control of the externally imposed forces and moments, the graph at 186 shows the rectified version of 184, and the graph at 188 shows the time average of 186 extracted using a low pass electronic filter.

Figure 19:
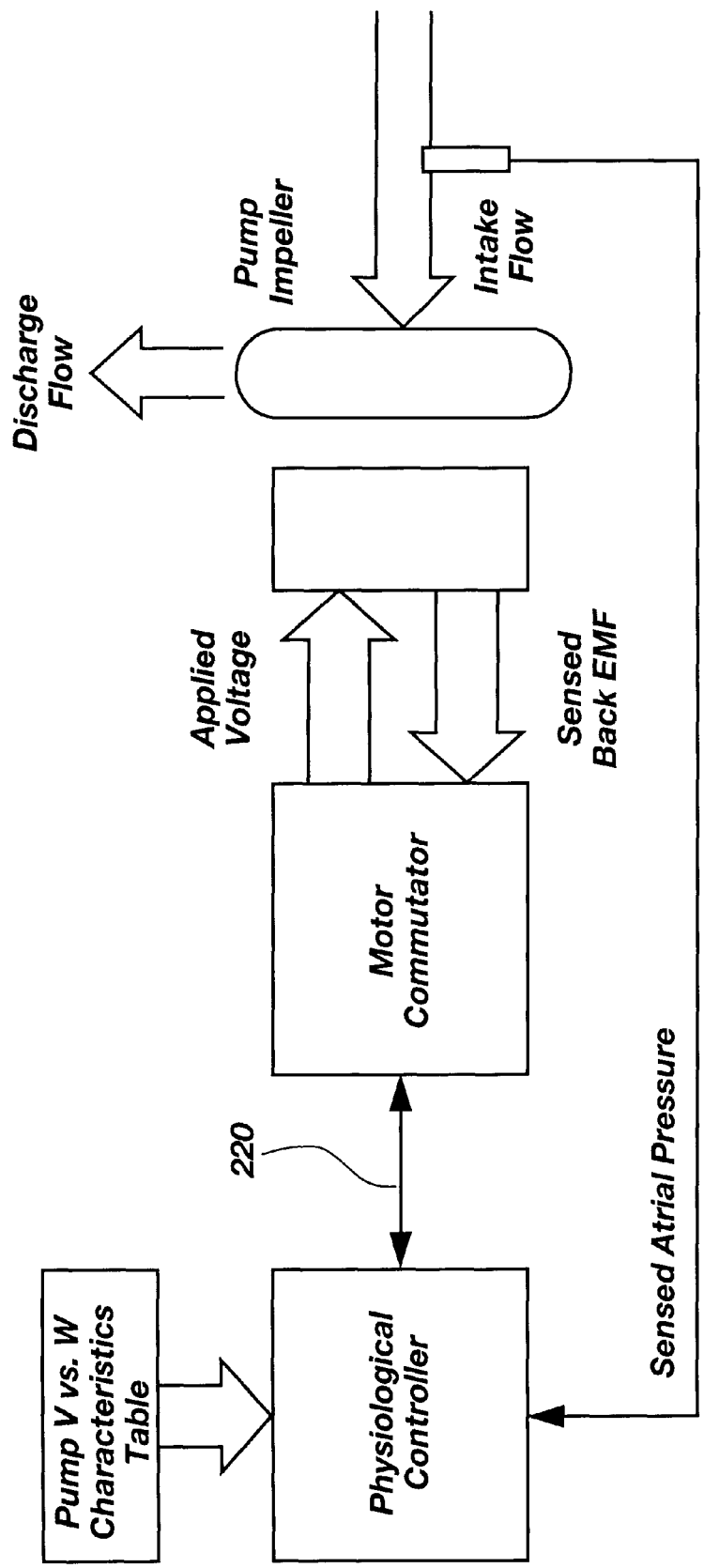
FIG. 19 shows a physiological electronic feedback control circuit for regulating the motor speed relative to preload and afterload signals.

FIG. 19 shows a circuit which extracts the change in coil current due to the control of the externally imposed forces and moments. This is shown in the preferred embodiment of a negative feedback circuit, which comprises an integrator whose gain is controlled by an analog multiplier indexed to the estimated gap. This feedback circuit includes a proportional-integral device where the estimated displacement and the integral of the estimated displacement are combined to form the negative feedback signal and then compared to the original voltage waveform to provide the desired current waveform proportional to the impeller displacement.

In this application, because of the permanent magnet arrangement, bias currents are not created that will produce high heat generation. Bias current is not desirable for use in human sensitive fluids such as blood. The axial thrust bearing is the one set of coils that uses the self sensing electronic controller and thus, hardware, circuit complexity, and wiring are all reduced along with the reduction in heat from bias currents.

The use of pumps for sensitive applications often requires adjustment of flow rates and pressure rises such as in the artificial heart where the physiological conditions change significantly. The rotational speed must never be so high as to cause excessive suction that can lead to inflow vessel collapse. For example, the body may be resting or sleeping with a rather low required flow rate and pressure rise whereas if the body is undergoing exercises, such as walking, a much higher flow rate and pressure rise is required. In one embodiment, the primary method of adjusting the flow rate and pressure rise is by varying the motor speed. In addition to the motor, the axial thrust bearings are the only set of coils (or magnetic forces) that are electrically controlled. Thus, although quadrants are unnecessary and the preferred embodiment does not have quadrants, the invention could use quadrants when additional moment control is desired or required.

A second embodiment of the physiological controller uses an indirect measurement of pressure rise from the inlet of the pump to the outlet of the pump (i.e., Pout−Pin). At a given flow rate, changes in pressure across the pump are an indication of changes in systemic resistance in the circulation system of the patient. Change in systemic resistance is known to be one indicator of increased physical exertion in humans. Thus, a measurement of pressure difference from outlet to inlet is used as a basis for a physiological controller.

The measurement of pressure difference from inlet to outlet can be indirectly measured by two methods which are (1) measurement of motor current and pump speed, or (2) measurement of bearing current, or some combination thereof. In physiological applications, the pump inlet pressure is called the preload while the pump exit pressure is called the afterload.

The first method to measure pressure indirectly uses measurements of motor current and pump speed. These measurements are used in an electronic controller to derive pressure based on equations and/or tables electronically stored in the controller. The relationship between current, speed, and pressure rise is characterized and calibrated prior to operation, providing the basis for the controller. The block diagram for the implementation of the controller is shown in FIG. 20.

The second method to measure pressure rise indirectly uses magnetic bearing current. It is well known that current in an active magnetic bearing is directly proportional to force on the rotor. The pressure difference from outlet to inlet of the pump can be derived directly from the resultant net force on the impeller due to the pressure difference. Hence, the bearing current can be used in an electronic controller to derive the pressure difference from outlet to inlet of the pump. The block diagram of the implementation of the controller is shown in FIG. 18.

FIG. 19, shows another embodiment of a physiological electronic feedback control circuit that is provided in the invention to regulate the motor speed relative to the preload and afterload signals thereby properly controlling the motor speed. The physiological control circuit is provided to regulate the pump flow rate and pressure rise to meet the physiological needs of the biological application. Reference number 220 indicates an interface between the physiological controller and the motor commutator such that a desired speed signal is sent to the motor commutator and an actual speed signal is sent to the physiological controller via voltage represented by the arrow in FIG. 22 designated as "Sensed Back EMF". Thus, the embodiment of FIG. 19 illustrates motor control based on physiological parameters.

In addition to electronic signals relating to the preload and afterload forces internal to the pump, the electronic signals from the activating coil currents in the electromagnetic bearings are related to other forces such as the gravitational loading and acceleration effects relating to the beginning of motion and the stopping of motion. Also, electronic signals related to the acceleration are obtained by sensing, either in the pump housing or other location of known position relative to the pump, the acceleration in one, two, or three orthogonal directions. The electronic acceleration signals are then employed in the invention to subtract that signal from the preload and afterload signals, as described above. The resulting difference signal is then used for the physiological controller described above.

The speed of the motor is related to the physiological performance of the pump. The motor feedback emf is used to sense the rotational speed of the motor rotating about the pump impeller axis and to develop an electronic signal proportional to the impeller rotational speed. The impeller rotational speed signal is provided to the electronic physiological feedback controller described above. The present motor rotational speed is used in combination withe the preload and afterload signals to adjust future motor speeds to match physiological pump flow rate and pressure rise needs based upon body requirements and to avoid undue suction.

The Method

Elements of construct 10 are operable in singular mode as a ventricular assist device, or paired for a total artificial heart. In the case of the total artificial heart which utilizes two of construct 10, each construct 10 operates entirely independent of the other construct, thereby eliminating complex control equipment and circuits that would otherwise be required if both constructs were combined.

The physiologic controller (not shown) senses fluid pressure inside intake vessel 19 and generates an electrical signal to modify rotational speed of motor 40 according to specific algorithms determined by electronic controller (not shown). The physiologic controller may signal a change in rotational speed of motor 40 to compensate for a change in fluid pressure inside intake vessel 19 yet avoid excessive rotational motor speed that would collapse vessels. In addition to controlling rotational speed of motor 40, the physiologic controller (not shown) senses position, velocity, and/or acceleration information of impeller 21 via eddy current, induction, optical, capacitance or other self-sensing electronic signals and generates an electrical signal that is sent to the electronic controller (not shown), which correspondingly provides adjustment to electrical current in electric activation coils 44 and 48, thereby providing adjustment to control forces exerted by electromagnetic thrust bearings 46 and 50. Adjustments to electromagnetic thrust bearings 46 and 50 compensates for applied forces due to fluid, motor forces, gravitational load, acceleration forces, and other incidental forces.

The rotation of impeller 21 brings impeller vanes 26 in contact with fluid to be pumped, thereby causing fluid to move radially toward spiral volute exit 18. The centrifugal transport of fluid from the region at the axial center of construct 10 toward the spiral volute exit 18 correspondingly creates a partial vacuum at the region of impeller intake opening 30 and draws in additional fluid through intake vessel 19. The unique logarithmic spiral configuration of spiral volute exit 18 then transports sensitive fluid along the region near the circumference of construct 10 in a smooth, non-turbulent and low thermal manner to outlet vessel 15. Outlet vessel 15 is connected to anatomical vessels or other mechanisms.

A portion of fluid pumped by impeller 21 returns from the region of high pressure near spiral volute 18 along both sides of impeller 21, via first impeller return chamber 32 and second impeller return chamber 34, in the form of reverse fluid flow to the region of lower pressure near impeller intake opening 30. Fluid returning along second impeller return chamber 34 also passes through impeller return opening 36, and thereby serves to equalize internal fluid pressures and prevent flow in the clearance passages from sensitive fluid stagnation.

If construct 10 is to be operated in pulsatile mode, rotational speed of impeller 21 is varied and controlled by the electronic controller (not shown), which adjust electrical current in motor 40, thereby accelerating and decelerating the rotation of impeller 21 and causing fluid to be pumped in a pulsatile fashion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. Apparatus for pumping sensitive biological fluids comprising:
   a construct having an exterior, a hollow interior having walls therein, at least one housing permanent magnet disposed therein, and an axial center;
   an inlet formed from the construct exterior for passage of fluids therethrough and into the hollow interior of the construct;
   an outlet formed from the construct exterior for passage of fluids therethrough from the hollow interior of the construct, the outlet radially located from the axial center of the construct;
   an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;
   a magnetic means comprising a plurality of electromagnetic actuators which provide six axes of control, including (i) one axial translational axis, (ii) two radial translational axes, and (iii) three rotational axes comprising two axes controlled for moment and one axis controlled by motor rotation, wherein at least one of the five axes controlled for moment, axial translation, and radial translation is controlled by a set of permanent magnets in the housing magnetized in an axis parallel to the axis of rotation of the impeller means, and further including at least one impeller permanent magnet juxtaposed to the housing permanent magnet for suspending the impeller means out of contact with the hollow interior of the construct; and
   a motor means for selectively rotating the impeller means to thereby control fluid flowing through the apparatus.

2. Apparatus of claim 1 wherein the construct comprises a first pump housing half and a second pump housing half hermetically sealed to the first pump housing half for forming the hollow interior of the construct.

3. Apparatus of claim 2 wherein the first pump housing half comprises a pump inlet vessel having an inlet throughbore, the pump inlet vessel forming the inlet within the construct exterior for passage of fluids therethrough and into the hollow interior of the construct.

4. Apparatus of claim 2 wherein the first and the second pump housing halves each include a protrusion wherein a pump outlet vessel having an outlet throughbore is formed from hermetically sealing said protrusions, the pump outlet vessel forming the outlet within the construct exterior for passage of fluids therethrough from the hollow interior of the construct.

5. Apparatus of claim 1 wherein the impeller means comprises an integrated combination of an impeller for fluid flow through the construct and a rotor being controlled by the motor means thereby allowing the motor means to control rotation of the impeller means, the integrated combination of the impeller and the rotor forming interior sides of a first return flow chamber and a second return flow chamber, respectively, for permitting fluid flow around the suspended impeller means.

6. Apparatus of claim 5 wherein the interior side of the rotor forming the second return flow chamber includes a second member having a curvature corresponding to a curvature of walls of the hollow interior of the construct, the second member being coupled to a first member by the arcuate blades of the impeller means wherein impeller chambers are formed from (i) the arcuate blades, (ii) the first member, and (iii) the second member, thus forming the arcuate passageways for the gradual redirection of fluid from the inlet to the outlet.

7. Apparatus of claim 6 wherein the second member includes a second magnetic material for interaction with a second electromagnetic thrust bearing and a second electric activation coil, wherein the second electromagnetic thrust bearing and the second electric activation coil stabilizes the impeller means and controls a combination of two degrees of freedom in radial position, axial position, external radial forces, and external thrust forces which act upon the impeller means.

8. Apparatus of claim 6 wherein the second member comprises a rotor integrally formed therein and the rotor having a plurality of permanent magnets disposed thereon for interaction with the motor means wherein the rotor may be rotated by the motor means and thereby rotate the impeller means.

9. Apparatus of claim 6 wherein the second member includes a second impeller permanent magnet for interaction with a second housing permanent magnet and a second impeller permanent magnet set for interaction with a second housing permanent magnet set, wherein (i) the second impeller permanent magnet is juxtaposed with the second housing permanent magnet such that a pole of the second impeller permanent magnet repels a pole of the second housing permanent magnet and (ii) the second impeller permanent magnet set is juxtaposed with the second housing permanent magnet set such that poles of the second impeller permanent magnet set repel poles of the second housing permanent magnet set thereby preventing contact between the second member and the housing.

10. Apparatus of claim 9 wherein the second impeller permanent magnetic set and the second housing permanent magnetic set each comprise a double ring configuration about the impeller and the housing, respectively, the double ring configuration of each magnetic set comprising a first magnetic ring and a second magnetic ring disposed in an attractive orientation with the first magnetic ring and the second impeller magnetic set disposed in reverse polarity with the second housing magnetic set.

11. Apparatus of claim 5 wherein the interior side of the impeller forming the first return flow chamber includes a first member having a curvature corresponding to a curvature of walls of the hollow interior of the construct.

12. Apparatus of claim 11 wherein the first member includes a first magnetic material for interaction with (i) a first electromagnetic thrust bearing and (ii) a first electric activation coil, wherein the first electromagnetic thrust bearing and the first electric activation coil stabilize the impeller means and permit a means for controlling a combination of an axial position, two degrees of freedom angular displacements, external thrust forces, and external moments which act upon the impeller means.

13. Apparatus of claim 11 wherein the first member includes a first impeller permanent magnet for interaction with a first housing permanent magnet and a first impeller permanent magnet set for interaction with a first housing permanent magnet set, wherein (i) the first impeller permanent magnet is juxtaposed with the first housing permanent magnet such that a pole of the first impeller permanent magnet repels a pole of the first housing permanent magnet and (ii) the first impeller permanent magnet set is juxtaposed with the first housing permanent magnet set such that poles of the first impeller permanent magnet set repel poles of the first housing permanent magnet set thereby preventing contact between the first member and the housing.

14. Apparatus of claim 13 wherein the first impeller magnetic set and the first housing magnetic set each comprise a multiple ring configuration about the impeller and the housing, respectively, the multiple ring configuration of each magnetic set comprising at least one first magnetic ring and at least one second magnetic ring disposed in an attractive orientation with the at least one first magnetic ring and the first impeller magnetic set disposed in reverse polarity with the first housing magnetic set.

15. Apparatus of claim 11 wherein the first member includes a hybrid combination of first impeller permanent magnet bearing and electromagnetic bearing sets for interaction with a first housing permanent magnet bearing and electromagnetic bearing sets such that each magnetic interaction creates a set of opposing forces and moments (torques) to the externally applied forces and moments applied to the impeller and, thus prevents contact between the first member and the housing and contributes to the suspension and stabilization of the impeller means.

16. Apparatus of claim 15 wherein the magnetic means includes:

positioning structure for controlling six axes of impeller motion, said positioning structure including a hybrid magnetic bearing system wherein the first impeller permanent magnetic bearing set and the first housing permanent magnetic bearing set each comprise a double permanent magnet ring situated about the impeller and the housing, with polarities arranged so that positive radial stiffnesses are generated, such that the impeller operates in a centered position relative to the two radial displacements for control of two of the six axes;

wherein a first impeller magnetic target set and the first housing electromagnetic bearing set comprise electromagnetic bearings which control the remaining axial displacement and two angular displacements of the six axes so that the impeller operates in a centered position with regard to the axial and two angular axes.

17. Apparatus of claim 15 wherein the magnetic means includes:

positioning structure for controlling six axes of impeller motion, said positioning structure including a hybrid magnetic bearing system wherein the first impeller permanent magnetic bearing set and the first housing permanent magnetic bearing set each comprise a double permanent magnet ring situated about the impeller and the housing, with polarities arranged so that positive radial stiffnesses are generated and soft magnetic iron is employed on one or more of the ring faces to focus the magnetic flux between the permanent magnet rings, such that the impeller operates in a centered position relative to the two radial displacements for control of two of the six axes;

wherein a first impeller magnetic target set and the first housing electromagnetic bearing set comprise electromagnetic bearings which control the remaining axial displacement and two angular displacements of the six axes so that the impeller operates in a centered position with regard to these three axes, a third angular axis being controlled by the motor means.

18. Apparatus of claim 15 wherein the magnetic means includes:

positioning structure for controlling six axes of impeller motion, said positioning structure including a hybrid magnetic bearing system wherein the first impeller permanent magnetic bearing set and the first housing permanent magnetic bearing set each comprise a set of multiple permanent magnet rings situated about the impeller and the housing, with polarities arranged so that positive radial stiffnesses are generated and soft magnetic iron is employee on at least one of the ring faces to focus the magnetic flux between the permanent magnet rings, such that the impeller operates in a centered position relative to the two radial displacements for control of two of the six axes;

wherein a first impeller magnetic target set and the first housing electromagnetic bearing set comprise electromagnetic bearings which control the remaining axial displacement and two angular displacements for control of three of the six axes so that the impeller operates in a centered position with regard to these three axes.

19. Apparatus of claim 15 wherein the magnetic means includes:

positioning structure for controlling six axes of impeller motion, said positioning structure including a hybrid magnetic bearing system wherein the first impeller permanent magnetic bearing set and the first housing permanent magnetic bearing set each comprise a set of multiple permanent magnet rings situated about the impeller and the housing, with polarities arranged so that positive radial stiffnesses and positive moment stiffness are generated and soft magnetic iron is employed on at least one of the ring faces to focus the magnetic flux between the permanent magnet rings, such that the impeller operates in a centered position relative to the two radial displacements and the two angular displacements for control of four of the six axes;

wherein a first impeller magnetic target set and the first housing electromagnetic bearing set comprise electromagnetic bearings which control the remaining axial displacement of the six axes so that the impeller operates in a centered position with regard to this axis.

20. Apparatus of claim 15 wherein the magnetic means includes:

positioning structure for controlling six axes of impeller motion, said positioning structure including a hybrid magnetic bearing system wherein the first impeller permanent magnetic bearing set and the first housing permanent magnetic set each comprise a set of multiples permanent magnet rings situated about the impeller and the housing, with polarities arranged so that positive axial stiffness and positive moment stiffnesses are generated and soft magnetic iron is employed on at least one of the ring faces to focus the magnetic flux between the permanent magnet rings, such that the impeller operates in a centered position relative to the axial displacement and the two angular displacements for control of three of the six axes; the first impeller magnetic target set and the electromagnetic bearings which control the remaining two radial displacements so that the impeller operates in a centered position with regard to these two axes.

21. Apparatus of claim 1 wherein the magnetic means comprises an arrangement of a first construct permanent magnet disposed on a first wall of the hollow interior of the construct, a second construct permanent magnet disposed on a second wall, opposite the first wall, of the hollow interior of the construct, a first impeller permanent magnet disposed on the impeller means distal to the axial center of the construct and juxtaposed with the first construct permanent magnet, a second impeller permanent magnet disposed on the impeller means distal to the axial center of the construct and juxtaposed with the second construct permanent magnet, a first construct permanent magnet set disposed on the first wall of the hollow interior of the construct, a second construct permanent magnet set disposed on the second wall of the hollow interior of the construct, a first impeller permanent magnet set disposed on the impeller means proximate to the axial center of the construct and juxtaposed with the first construct permanent magnet set, and a second impeller permanent magnet set disposed on the impeller means proximate to the axial center of the construct and juxtaposed with the second construct permanent magnet set, wherein the arrangement provides radial stabilization and, due to angular positioning, provides a degree of translational stabilization of the impeller means and the impeller means is prevented from contacting the hollow interior of the construct by magnetic fields.

22. Apparatus of claim 21 wherein the arrangement further comprises self correcting positioning means for dynamically positioning the impeller means during operation such that the impeller means is constantly out of contact with the construct.

23. Apparatus of claim 21 wherein the magnetic means includes at least one coil disposed in the first wall of the construct housing and at least another one coil disposed in the second wall of the construct housing, the at least one coil being juxtaposed between (i) the first construct permanent magnet and (ii) the first construct permanent magnet set, and the at least another one coil being juxtaposed between (i) the second construct permanent magnet and (ii) the second construct permanent magnet set, at least one electromagnetic thrust bearing disposed in the construct housing about the at least one coil and the at least another one coil, and an electronic controller for controlling electric current in the at least one coil and the at least another one coil thereby causing changes in forces exerted by the at least one electromagnetic thrust bearing.

24. Apparatus of claim 23, further comprising a physiological controller for controlling a rate of rotation of the impeller so that the rate of rotation corresponds to the physiological state of a person using the apparatus of the present invention, said physiological controller being coupled to the electronic controller, said electronic controller further including means for monitoring change of electronic parameters selected from the group consisting of (i) bearing currents in the at least one electromagnetic thrust bearing, (ii) bearing voltages in the at least one electromagnetic thrust bearing, (iii) motor currents, and (iv) motor voltages.

25. Apparatus of claim 1 wherein the motor means comprises a stator integrally formed within a wall of the hollow interior of the construct, the stator having windings fixed therein for receiving current from a motor controller.

26. Apparatus of claim 1 wherein the motor means comprises a rotor having a circumference integrally formed as part of the impeller means, the rotor having a plurality of permanent magnets disposed therein such that (i) poles of the plurality of permanent magnets alternate between north and south and (ii) the plurality of permanent magnets are arranged to form a circular pattern concentric with the circumference of the rotor.

27. An apparatus as defined in claim 1, further comprising a plurality of electromagnetic segments which are individually controlled to provide the six axes of control.

28. A continuous flow pump for pumping sensitive biological fluids comprising:

a construct having a first pump housing half and a second pump housing half hermetically sealed to the first pump housing half to form the construct, the construct having a hollow interior and an axial center;

a pump inlet vessel formed from the first pump housing half and having an inlet throughbore for passage of fluids therethrough and into the hollow interior of the construct;

a pump outlet vessel radially located from the axial center of the construct and formed from the first and second pump housing halves and having an outlet throughbore for passage of fluids therethrough from the hollow interior of the construct;

an impeller means disposed within the hollow interior of the construct and out of contact therewith and having an impeller intake opening, impeller chambers, and impeller vanes having a spiral curvature for forming the impeller chambers, the impeller means for controlling fluid flow into the pump inlet vessel, through the hollow interior of the cavity, and out of the pump outlet vessel;

a magnetic means comprising a plurality of electromagnetic actuators to provide six axes of control, including (i) one axial translational axis, (ii) two radial translational axes, and (iii) three rotational axes comprising two axes controlled for moment and one axis controlled by motor rotation, wherein at least one of the five axes controlled for moment, axial translation, and radial translation is controlled by a set of permanent magnets in the housing magnetized in an axis parallel to the axis of rotation of the impeller means, said electromagnetic actuators being positioned for suspending the impeller means out of contact with the hollow interior of the construct and for selectively rotating the impeller means to thereby control fluid flowing through the continuous flow pump; and a motor means for controlling rotational speed of the impeller means.

29. A method for pumping sensitive biological fluids using a pump comprising the steps of:

selecting a pump device having a magnetically suspended impeller within a housing of the pump having at least one permanent magnet disposed therein, the impeller having arcuately shaped vanes for reducing impact on the sensitive fluids traveling through the pump;

positioning the impeller within the housing according to signals received from magnetic means that are used to magnetically suspend the impeller;

controlling a plurality of electromagnetic actuators to provide six axes of control, including (i) one axial translational axis, (ii) two radial translational axes, and (iii) three rotational axes comprising two axes controlled for moment and one axis controlled by motor rotation;

positioning the electromagnetic actuators such that at least one of the five axes controlled for moment, axial translation, and radial translation is controlled by a set of permanent magnets in the housing magnetized in an axis parallel to the axis of rotation of the impeller means; and adjusting the impeller rotational speed and thus the rate of fluid flow according to signals received frog an input and an output of the pump.

30. Apparatus of claim 13 wherein the first impeller magnetic set and the first housing magnetic set each comprise a double ring configuration about the impeller and the housing, respectively, the double ring configuration of each magnetic set comprising a first magnetic ring and a second magnetic ring disposed in an attractive orientation with the first magnetic ring and the first impeller magnetic set disposed in reverse polarity with the first housing magnetic set.

31. Apparatus for pumping sensitive biological fluids comprising:

a construct having an exterior, a hollow interior having walls therein, at least one housing permanent magnet disposed therein, and an axial center;

an inlet formed from the construct exterior for passage of fluids therethrough and into the hollow interior of the construct;

an outlet formed from the construct exterior for passage of fluids therethrough from the hollow interior of the construct, the outlet radially located from the axial center of the construct;

an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;

a magnetic means including at least one impeller permanent magnet juxtaposed to the housing permanent magnet for suspending the impeller means out of contact with the hollow interior of the construct; and a motor means for selectively rotating the impeller means to thereby control fluid flowing through the apparatus, said motor means including stator windings formed within the housing of the construct and arcuately shaped permanent magnets with a soft iron core formed as part of the impeller means, said permanent magnets and soft iron core arranged such that magnetic flux is present on only one side of the rotor, interacting with stator windings on the same side.

32. Apparatus for pumping sensitive biological fluids comprising:

a construct having an exterior, a hollow interior having walls therein, at least one housing permanent magnet disposed therein, and an axial center;

an inlet formed from the construct exterior for passage of fluids therethrough and into the hollow interior of the construct;

an outlet formed from the construct exterior for passage of fluids therethrough from the hollow interior of the construct, the outlet radially located from the axial center of the construct;

an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;

a magnetic means including at least one impeller permanent magnet juxtaposed to the housing permanent magnet for suspending the impeller means out of contact with the hollow interior of the construct; and a motor means for selectively rotating the impeller means to thereby control fluid flowing through the apparatus;

wherein the impeller means comprises an integrated combination of an impeller for fluid flow through the construct and a rotor being controlled by the motor means thereby allowing the motor means to control rotation of the impeller means, the integrated combination of the impeller and the rotor forming interior sides of a first return flow chamber and a second return flow chamber, respectively, for permitting fluid flow around the suspended impeller means;

wherein the interior side of the impeller forming the first return flow chamber includes a first member having a curvature corresponding to a curvature of walls of the hollow interior of the construct; and wherein the first member includes a first impeller permanent magnet for interaction with a first housing permanent magnet and a first impeller permanent magnet set for interaction with a first housing permanent magnet set, wherein (i) the first impeller permanent magnet is juxtaposed wits the first housing permanent magnet such that a pole of the first impeller permanent magnet repels a pole of the first housing permanent magnet and (ii) the first impeller permanent magnet set is juxtaposed with the first housing permanent magnet set such that poles of the first impeller permanent magnet set repel poles of the first housing permanent magnet set thereby preventing contact between the first member and the housing; and wherein the first impeller magnetic set and the first housing magnetic set each comprise a multiple ring configuration about the impeller and the housing, respectively, the multiple ring configuration of each magnetic set comprising at least one first magnetic ring and at least one second magnetic ring disposed in an attractive orientation with the at least one first magnetic ring and the first impeller magnetic set disposed in reverse polarity with the first housing magnetic set.

33. Apparatus for pumping sensitive biological fluids comprising:

a construct having an exterior, a hollow interior having walls therein, at least one housing permanent magnet disposed therein, and an axial center;

an inlet formed from the construct exterior for passage of fluids therethrough and into the hollow interior of the construct;

an outlet formed from the construct exterior for passage of fluids therethrough from the hollow interior of the construct, the outlet radially located from the axial center of the construct;

an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;

a magnetic means including at least one impeller permanent magnet juxtaposed to the housing permanent magnet for suspending the impeller means out of contact with the hollow interior of the construct; and a motor means for selectively rotating the impeller means to thereby control fluid flowing through the apparatus;

wherein the impeller means comprises an integrated combination of an impeller for fluid flow through the construct and a rotor being controlled by the motor means thereby allowing the motor means to control rotation of the impeller means, the integrated combination of the impeller and the rotor forming interior sides of a first return flow chamber and a second return flow chamber, respectively, for permitting fluid flow around the suspended impeller means;

wherein the interior side of the rotor forming the second return flow chamber includes a second member having a curvature corresponding to a curvature of walls of the hollow interior of the construct, the second member being coupled to a first member by the arcuate blades of the impeller means wherein impeller chambers are formed from (i) the arcuate blades, (ii) the first member, and (iii) the second member, thus forming the arcuate passageways for the gradual redirection of fluid from the inlet to the outlet;

wherein the second member includes a second impeller permanent magnet for interaction with a second housing permanent magnet and a second impeller permanent magnet set for interaction with a second housing permanent magnet set, wherein (i) the second impeller permanent magnet is juxtaposed with the second housing permanent magnet such that a pole of the second impeller permanent magnet repels a pole of the second housing permanent magnet and (ii) the second impeller permanent magnet set is juxtaposed with the second housing permanent magnet set such that poles of the second impeller permanent magnet set repel poles of the second housing permanent magnet set thereby preventing contact between the second member and the housing; and wherein the second impeller permanent magnetic set and the second housing permanent magnetic set each comprise a double ring configuration about the impeller and the housing, respectively, the double ring configuration of each magnetic set comprising a first magnetic ring and a second magnetic ring disposed in an attractive orientation with the first magnetic ring and the second impeller magnetic set disposed in reverse polarity with the second housing magnetic set.

34. Apparatus for pumping sensitive biological fluids comprising:

a construct having an exterior, a hollow interior having walls therein, at least one housing permanent magnet disposed therein, and an axial center;

an inlet formed from the construct exterior for passage of fluids therethrough and into the hollow interior of the construct;

an outlet formed from the construct exterior for passage of fluids therethrough from the hollow interior of the construct, the outlet radially located from the axial center of the construct;

an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;

a magnetic means including at least one impeller permanent magnet juxtaposed to the housing permanent magnet, which is magnetized in an axis parallel to the axis of rotation of the impeller means for suspending the impeller means out of contact with the hollow interior of the construct; and a motor means for selectively rotating the impeller means to thereby control fluid flowing through the apparatus.

* * * * *